United States Patent
Borner et al.

(10) Patent No.: US 7,230,134 B2
(45) Date of Patent: Jun. 12, 2007

(54) METHOD FOR THE PRODUCTION OF AMINES BY REDUCTIVE AMINATION OF CARBONYL COMPOUNDS UNDER TRANSFER-HYDROGENATION CONDITIONS

(75) Inventors: Armin Borner, Rostock (DE); Uwe Dingerdissen, Seeheim (DE); Renat Kadyrov, Frankfurt (DE); Thomas Riermeier, Nidderau-Ostheim (DE); Vitali Tararov, Moskau (RU)

(73) Assignee: Degussa AG, Dusseldorf (DE)

( * ) Notice: Subject to any disclaimer, the term of this patent is extended or adjusted under 35 U.S.C. 154(b) by 150 days.

(21) Appl. No.: 10/484,900

(22) PCT Filed: Aug. 6, 2002

(86) PCT No.: PCT/EP02/08748

§ 371 (c)(1),
(2), (4) Date: Aug. 18, 2004

(87) PCT Pub. No.: WO03/014061

PCT Pub. Date: Feb. 20, 2003

(65) Prior Publication Data

US 2004/0267051 A1  Dec. 30, 2004

(30) Foreign Application Priority Data

Aug. 9, 2001 (DE) ............... 101 38 140

(51) Int. Cl.
*C07C 209/28* (2006.01)

(52) U.S. Cl. ............ 564/398; 564/397; 564/472; 564/473

(58) Field of Classification Search ............ None
See application file for complete search history.

(56) References Cited

U.S. PATENT DOCUMENTS

| 4,851,548 A | 7/1989 | Hay |
| 5,338,885 A | 8/1994 | Immel et al. |
| 5,514,358 A * | 5/1996 | Rogers et al. .......... 423/352 |

FOREIGN PATENT DOCUMENTS

| EP | 0 535 484 | 4/1993 |

OTHER PUBLICATIONS

Chemical Abstracts, vol. 53, No. 4, Feb. 25, 1959 Patent Abstract, "Synthesis of Amines by the Method of Leuckart".

* cited by examiner

*Primary Examiner*—Brian Davis
(74) *Attorney, Agent, or Firm*—Smith, Gambrell & Russell, LLP

(57) ABSTRACT

This application claims the benefit of German priority Application No. 10138140.9, filed on Aug. 9, 2001, and International Application No. PCT/EP02/08748, filed on Aug. 6, 2002. The invention relates to the production of amines by the reaction of aldehydes or ketones with ammonia or primary or secondary amines in the presence of a hydrogen-donor and the presence of homogeneous metal catalysts of the eighth sub-group under mild conditions.

19 Claims, No Drawings

METHOD FOR THE PRODUCTION OF AMINES BY REDUCTIVE AMINATION OF CARBONYL COMPOUNDS UNDER TRANSFER-HYDROGENATION CONDITIONS

This application claims the benefit of German priority Application No. 10138140.9, filed on Aug. 9, 2001, and International Application No. PCT/EP02/08748, filed on Aug. 6, 2002.

FIELD OF THE INVENTION

The invention describes the production of amines by the reaction of aldehydes or ketones with ammonia or primary or secondary amines in the presence of a hydrogen donor and in the presence of homogeneous metal catalysts under mild conditions.

BACKGROUND OF THE INVENTION

Racemic and enantiomerically pure amines play a dominant role in numerous complex natural substances, such as e.g. the alkaloids, vitamins or amino acids, the chemical, pharmaceutical and industrial importance of which is undisputed. As chemical intermediates, amines find applications in the synthesis of pharmaceuticals, agrochemicals, food additives, colours or cosmetics, among other sectors. For the active substances sector, amino acids and amino alcohols play a dominant role.

For the synthesis of non-functionalised and functionalised amines, the reductive amination (hydroamination) of ketones and aldehydes plays a large part. Considerable preparative and technical importance is attached to catalytic reduction with hydrogen (W. S. Emerson in *Organic Reactions*, Vol. 4, John Wiley & Sons, New York, 1948, pp. 174–255, Rylander *Catalytic Hydrogenation over Platinum Metals*, Academic Press, New York, 1967, pp. 291–303; Catalytic Hydrogenation in Organic Synthesis, Academic Press, New York, 1979, 165 ff; M. V. Klyuev, M. L. Khidekel *Ruiss. Chem. Rev.* 1980, 49, 14–27; Rylander *Hydrogenation Methods*; Academic Press, New York, 1985, pp. 82–93; V. A. Tarasevich, N. G. Kozlov *Ruiss. Chem. Rev.* 1999, 68, 55–72). The use of hydrogen as a reducing agent requires high-pressure apparatus, which involve high operating costs and represent considerable technical complexity in the construction and operation of suitable plants.

Reductions with metal hydrides, such as sodium borohydride (G. W. Gribble *Chem. Soc. Rev.* 1998, 27, 395–404), sodium cyanoborohydride (R. O. Hutchins, N. R. Natale *Org. Prep. Proceed. Int.* 1979, 11, 201) or sodium triacetoxyborohydride (A. F. Abdel-Magid, C. A. Maryanoff in Reductions in Organic Synthesis, ACS Symp. Ser. Vol. 641, 1996, 201–216), generally take place under milder conditions, but are associated with considerable problems such as risk of explosion and toxicity.

Other reducing agents, such as aluminium or zinc (F. Möller, R. Schröter in Houben-Weyl, Methoden der Organischen Chemie, vol. XI/1, ed. E. Muller; Thieme Verlag, Stuttgart, 1957, 667–669), and electrolytic reduction (Yu. D. Smirnov, L. A. Fedorova, A. P. Tomilov *Elektrokhimia* 1992, 28, 588–599), are of lesser importance. The production of chiral amines in this case requires the use of stoichiometric quantities of chiral auxiliary compounds, which are often difficult to obtain, and usually their subsequent separation. Very high optical yields are achieved in enzymatic transamination (R. O. Duthaler *Tetrahedron.* 1994, 50, 1539–1650). However, the method is mainly restricted to the production of amino acids. In addition, the corresponding amines can be obtained only with difficulty. Furthermore, the separation of the aqueous buffer solutions involves high costs.

In reductive amination according to Leuckart-Wallach (M. L. Moore in *Organic Reactions*, Vol. 5, John Wiley & Sons, New York, 1949, pp. 301–330), formic acid is used as the reducing agent. On a laboratory scale, the use of the easy to handle organic hydrogen donors as reducing agents is well proven, as these are non-explosive and of low toxicity. By varying these hydrogen donors, the selectivity of the amination reaction can also be influenced. The Leuckart-Wallach reaction is accelerated by adding support-bound, heterogeneous hydrogenation catalysts such as nickel or cobalt (A. N. Kost *Nauch. Doklady Vysshei Shkoly, Khim. I Khim. Tekhnol.* 1958, 125–129, C. A. 1959, 53, 3112i), nickel-aluminium alloys or Raney nickel (DRP 861844 (1943), *Chem. Zentralblatt,* 1953, 5926).

Lewis acids, such as magnesium chloride, zinc chloride, iron chloride (J. F. Bunnett, J. L. Marks *J. Am. Chem. Soc.* 1949, 71, 1587–1589) or aluminium chloride (U.S. Pat. No. 4,851,548) also catalyse the amination of carbonyl compounds. In this case, the reaction of ketones only takes place with satisfactory yields at high temperatures of 150 to 200° C. With the catalysts described, however, it is not possible to perform an enantioselective reaction.

SUMMARY OF THE INVENTION

The invention is therefore based on the object of providing a catalytic process with which the amination of carbonyl compounds is made possible under mild conditions and which enables enantiomerically pure or enantiomer-enriched amines to be synthesised if necessary.

Surprisingly, it has now been found that the desired amines can be obtained very efficiently by reductive hydride transfer amination of ketones and aldehydes with ammonia, primary or secondary amines in the presence of a hydrogen donor and of catalytically active transition metal complexes containing at least one metal from the group Fe, Ru, Os, Co, Rh, Ir, Ni, Pd, Pt under very mild conditions. Homogeneous metal atom-ligand complexes with central atoms from the group Ru or Rh are preferably used.

DESCRIPTION OF THE INVENTION

The mild reaction conditions enable carbonyl compounds with many different structures to be used as educt for reductive hydride transfer amination. In addition, because of the mild conditions, when chiral ligands are used it is possible to perform an enantioselective reaction. The transition metal catalysts employed from the eighth subgroup provide good to very good yields of desired amine in reductive amination. At the same time, a very high amine/alcohol ratio can be achieved in the products.

As educts, for example, carbonyl compounds of the formula (I)

can be reacted with ammonia, primary or secondary amines of the formula (II)

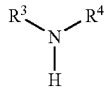

(II)

to form compounds of the general formula (III),

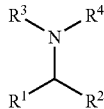

(III)

wherein the residues $R^1$ to $R^4$, independently of one another, can be selected from the group of hydrogen, $(C_1–C_{24})$-alkyl, $(C_2–C_{24})$-alkenyl, $(C_2–C_{24})$-alkynyl; $(C_5–C_{10})$-aryl, $CF_3$, CHO, CO-alkyl-$(C_1–C_8)$, CO-aryl-$(C_5–C_{10})$, COO-alkyl-$(C_1–C_8)$, COO-aryl-$(C_5–C_{10})$, $C(=N$-alkyl-$(C_1–C_8))$O-alkyl-$(C_1–C_8)$, $C(=N$-aryl-$(C_6–C_{10}))$O-alkyl-$(C_1–C_8)$, $C(=N$-alkyl-$(C_1–C_8))$O-aryl-$(C_5–C_{10})$, $C(=N$-aryl-$(C_5–C_{10}))$O-aryl-$(C_5–C_{10})$, $CONH_2$, CONH alkyl-$(C_1–C_8)$, CON(alkyl-$(C_1–C_8))_2$, CONH-aryl-$(C_5–C_{10})$, CON(aryl-$(C_5–C_{10}))_2$, PO(aryl-$(C_5–C_{10}))_2$, PO(alkyl-$(C_1–C_4))_2$, PO(alkyl-$(C_1–C_4))$ (O-alkyl-$(C_1–C_6))$, PO(alkyl-$(C_1–C_6))$ (O-aryl-$(C_5–C_{10}))$, PO(aryl-$(C_5–C_{10}))$ (O-alkyl-$(C_1–C_6))$, PO(O-alkyl-$(C_1–C_6))_2$, PO(O-aryl-$(C_5–C_{10}))_2$, PO(O-alkyl-$(C_1–C_6))$(O-aryl-$(C_5–C_{10}))$, $SO_2$—O-alkyl-$(C_1–C_4)$, $SO_2$—O-aryl-$(C_5–C_{10})$, $SO_2$-alkyl-$(C_1–C_6)$, $SO_2$-aryl-$(C_5–C_{10})$, SO-alkyl-$(C_1–C_8)$, SO-aryl-$(C_5–C_{10})$ or Si(alkyl-$(C_1–C_8))_3$, Si$(C_1–C_{10}$-alkyl/$C_5–C_{10}$-aryl)$_3$, wherein M represents a cation, e.g. a $Li^+$, $Na^+$, $K^+$, $Mg^{2+}$, $Ca^{2+}$, $NH_4^+$, $N(C_{1–C11}$-alkyl)$_4$, $N(H/C_1–C_{10}$-alkyl/$C_6–C_{10}$-aryl)$_4^+$, and/or $R^1$ to $R^2$, independently of one another, can be selected from the group CH(O-alkene-$(C_2–C_8)$—O), C(O-alkene-$(C_2–C_8)$-O)-alkyl-$(C_1–C_8)$, C(O-alkene-$(C_2–C_8)$—O)-aryl-$(C_5–C_{10})$, CH(O-alkyl-$(C_1–C_8))_2$, C(O-alkyl-$(C_1–C_8))_2$-alkyl-$(C_1–C_8)$, C(O-alkyl-$(C_1–C_8))_2$-aryl-$(C_5–C_{10})$, CHO, CN, COOH, COOM, POH(alkyl-$(C_1–C_6))$, POH(aryl-$(C_5–C_{10}))$, $PO_3H_2$, $PO_3M_2$, $SO_3H$, $SO_3M$, wherein M represents a cation, e.g. a $Li^+$, $Na^+$, $K^+$, $Mg^{2+}$, $Ca^{2+}$, $NH_4^+$, $N(C_1–C_{10}$-alkyl)$_4^+$, $N(H/C_1–C_{10}$-alkyl/$C_6–C_{10}$-aryl)$_4^+$, and/or $R^3$ and $R^4$, independently of one another, can be selected from the group O-alkyl-$(C_1–C_8)$, O-aryl-$(C_5–C_{10})$, fluorine, OH, $NH_2$, NH(alkyl-$(C_1–C_8))$, N(alkyl-$(C_1–C_8))_2$, NH(aryl-$(C_5–C_{10}))$, NHCO-alkyl-$(C_1–C_4)$, NHCO-aryl-$(C_5–C_{10})$, NHCOO-alkyl-$(C_1–C_8)$, NHCOO-aryl-$(C_5–C_{10})$, wherein alkyl denotes a linear or branched, aliphatic or cyclic residue, alkenyl denotes an olefinic hydrocarbon, alkynyl denotes an acetylene hydrocarbon and aryl denotes an aromatic residue, wherein up to 4 carbon atoms can be replaced by a nitrogen, phosphorus, silicon, sulfur or oxygen atom in each case.

The heteroaliphatic or heteroaromatic groups of the educts preferably contain one or two nitrogen atoms or an oxygen, sulfur or phosphorus atom.

Examples of particularly preferred alkyl groups or heterocycloalkyl groups are methyl, ethyl, n-propyl, iso-propyl, n-butyl, iso-butyl, sec-butyl, t-butyl-, cyclopentyl, cyclohexyl, tetrahydrofuryl, tetrahydropyryl, tetrahydrothiophenyl, piperidinyl, morpholinyl and phosphorinanyl residues.

Examples of particularly preferred aryl groups or heteroaryl groups are cyclopentadienyl anion, phenyl, naphthyl, pyrrolyl, imidazolyl, thiophenyl, pyridyl, pyrimidyl, indolyl and quinolinyl residues.

The alkyl, alkenyl, alkynyl, aryl, heterocycloalkyl and heteroaryl groups can carry substituents, in addition to hydrogen also $(C_1–C_{20})$-alkyl, $(C_2–C_{20})$-alkenyl, $(C_1–C_{10})$-haloalkyl, $(C_{3–C8})$-cycloalkyl, $(C_{5–C8})$-cycloalkenyl, $(C_{2–C9})$-heterocycloalkyl, $(C_1–C_9)$-heterocycloalkenyl, $(C_5–C_{14})$-aryl, $(C_2–C_{13})$-heteroaryl, wherein the number of heteroatoms selected from the group N, O, S, can be one to four, fluorine, chlorine, bromine, iodine, OH, $NO_2$, $CF_3$, O-alkyl-$(C_1–C_8)$, O-aryl-$(C_5–C_{10})$, OCOH, OCO-alkyl-$(C_1–C_8)$, OCO-alryl-$(C_5–C_{10})$, $NH_2$, NH(alkyl-$(C_1–C_8))$, NH(aryl-$(C_5–C_{10}))$, N(alkyl-$(C_1–C_8))_2$, N(aryl-$(C_5–C_{10}))_2$, NHCO-alkyl-$(C_1–C_8)$, NHCO-aryl-$(C_5–C_{10})$, NHCOH, NHCOO-alkyl-$(C_1–C_4)$, NHCOO-aryl-$(C_5–C_{10})$, CH(O-alkene-$(C_2–C_8)$—O), C(O-alkene-$(C_2–C_8)$—O)-alkyl-$(C_1–C_8)$, C(O-alkene-$(C_2–C_8)$—O)-aryl-$(C_5–C_{10})$, CH(O-alkyl-$(C_1–C_8))_2$, C(O-alkyl-$(C_1–C_8))_2$-alkyl-$(C_1–C_8)$, C(O-alkyl-$(C_1–C_8))_2$-aryl-$(C_5–C_{10})$, CHO, CO-alkyl-$(C_1–C_8)$, CO-aryl-$(C_5–C_{10})$, CN, COOH, COOM, COO-alkyl-$(C_{1–C8})$, COO-aryl-$(C_{5–C10})$, $C(=N$-alkyl-$(C_1–C_8))$O-alkyl-$(C_1–C_8)$, $C(=N$-aryl-$(C_5–C_{10}))$O-alkyl-$(C_1–C_8)$, $C(=N$-alkyl-$(C_1–C_8)$O-aryl-$(C_5–C_{10})$, $C(=N$-aryl-$(C_5–C_{10}))$(O-aryl-$(C_5–C_{10}))$, $CONH_2$, CONH-alkyl-$(C_1–C_8)$, CON(alkyl-$(C_1–C_8))_2$, CONH-aryl-$(C_5–C_{11})$, CON(aryl-$(C_5–C_{10}))_2$, $CHCHCO_2H$, CHCH—COO-alkyl-$(C_1–C_8)$, P(aryl-$(C_5–C_{10}))_2$, P(alkyl-$(C_1–C_8))_2$, PO(aryl-$(C_5–C_{10}))_2$, PO(alkyl-$(C_1–C_4))_2$, $PO_3H_2$, $PO_3M_2$, PO-alkyl-$(C_1–C_4)$(O-alky-$(C_1–C_6))$, PO(O-alkyl-$(C_1–C_6))_2$, OPO(aryl-$(C_5–C_{10}))_2$, OPO(alkyl-$(C_1–C_4))_2$, OPOH(alkyl-$(C_1–C_6))$, $OPO_3H_2$, $OPO_3M_2$, OPO-alkyl-$(C_1–C_4)$(O-alkyl-$(C_1–C_6))$, OPO(O-alkyl-$(C_1–C_6))_2$, OPO(O-aryl)$_2$—$(C_5–C_{10})$, $SO_3H$, $SO_3M$, $SO_3$-alkyl-$(C_1–C_4)$, $SO_2$-alkyl-$(C_1–C_6)$, SO-alkyl-$(C_1–C_6))$, $OSO_3H$, $OSO_3M$, $OSO_2$—O-alkyl-$(C_1–C_4)$, $OSO_2$-alkyl-$(C_1–C_6)$ or Si(alkyl-$(C_1–C_8))$ $_3$, Si $(C_1–C_8$-alkyl/$C_5–C_{10}$-aryl)$_3$, wherein M represents a cation selected from the group $Li^+$, $Na^+$, $K^+$, $Mg^{2+}$, $Ca^{2+}$, $NH_4^+$, $N(C_1–C_{10}$-alkyl)$_4^+$, $N(H/C_1–C_{10}$-alkyl/$C_5–C_{10}$-aryl)$_4^+$.

Both $R^1$ and $R^2$, and $R^3$ and $R^4$, can be linked by covalent bonds, so that $R^1$ and $R^2$, and $R^3$ and $R^4$, each form a saturated or unsaturated carbocyclic unit having 3 to 15 atoms, preferably 3 to 8 atoms, or a corresponding heterocyclic unit with one to four nitrogen, phosphorus, silicon, sulfur or oxygen atoms. An intramolecular reaction with ring closure is also possible by covalent linking of $R^3/R^1$.

Particularly preferred substituents $R^1$ and $R^2$ are hydrogen, $(C_1–C_{12})$-alkyl, $(C_2–C_{12})$-alkenyl, $(C_2–C_{12})$-alkynyl, $(C_5–C_{10})$-aryl, $CF_3$, CHO, CO-alkyl-$(C_1–C_8)$, CO-aryl-$(C_5–C_{10})$, CH(O-alkene-$(C_2–C_4)$—O), C(O-alkene-$(C_2–C_4)$—O)-alkyl-$(C_1–C_8)$, C(O-alkene-$(C_2–C_4)$—O)-aryl-$(C_5–C_{10})$, CH(O-alkyl-$(C_1–C_8))_2$, C(O-alkyl-$(C_1–C_8))_2$-alkyl-$(C_1–C_8)$, C(O-alkyl-$(C_1–C_8))_2$-aryl-$(C_5–C_{10})$, CN, COOH, COOM, COO-alkyl-$(C_1–C_8)$, COO-aryl-$(C_5–C_{10})$, $C(=N$-alkyl-$(C_1–C_8))$O-alkyl-$(C_1–C_8)$, $C(=N$-aryl-$(C_5–C_{10}))$O-alkyl-$(C_1–C_8)$, $C(=N$-alkyl-$(C_1–C_8))$(O-aryl-$(C_5–C_{10}))$, $C(=N$-aryl-$(C_5–C_{10}))$O-aryl-$(C_5–C_{10})$, $CONH_2$, CONH-alkyl-$(C_1–C_8)$, CON(alkyl-$(C_1–C_8))_2$, CONH-aryl-$(C_{5–C10})$, PO(aryl-$(C_5–C_{10}))_2$, PO(alkyl-($C_1$–$C_4$))$_2$, POH(alkyl-($C_1$–$C_6$)), POH(aryl-($C_5$–$C_{10}$)), PO(alkyl-($C_1$–$C_4$))(O-alkyl-($C_1$–$C_6$)), PO(alkyl-($C_{1–C6}$))(O-aryl-($C_5$–$C_{10}$)), PO (aryl-($C_5$–$C_{10}$))(O-alkyl-($C_{1–C6}$)), PO$_3$H$_2$, PO$_3$M$_2$, PO(O-alkyl-($C_1$–$C_6$))$_2$, PO(O-aryl-($C_5$–$C_{10}$))$_2$, PO(O-alkyl-($C_1$–$C_6$))(O-aryl-($C_5$–$C_{10}$)), SO$_3$H, SO$_3$M, SO$_2$—O-alkyl-($C_1$–$C_4$), SO$_2$—O-aryl-($C_5$–$C_{10}$), SO$_2$-alkyl-($C_1$–$C_6$), SO$_2$-aryl-($C_5$–$C_{10}$), SO-alkyl-($C_1$–$C_8$), SO-aryl-($C_5$–$C_{10}$) or Si(alkyl-($C_{1–C8}$))$_3$, Si($C_1$–$C_{10}$alkyl/$C_5$–$C_{10}$-aryl)$_3$, wherein M is a cation selected from the group Li$^+$, Na$^+$, K$^+$, Mg$^{2+}$, Ca$^{2+}$, NH$_4^+$, N($C_1$–$C_{10}$-alkyl)$_4^+$, N($C_{1–C10}$-alkyl/$C_5$–$C_{10}$-aryl)$_4^+$.

Particularly preferred substituents R$^3$ and R$^4$ are hydrogen, ($C_1$–$C_{12}$)-alkyl, ($C_2$–$C_{12}$)-alkenyl, ($C_2$–$C_{12}$)-alkynyl, ($C_5$–$C_{10}$)-aryl, O-alkyl-($C_1$–$C_8$), O-aryl-($C_{5–C12}$), OH, NH$_2$, NH(alkyl-($C_1$–$C_8$)), N(alkyl-($C_1$–$C_8$))$_2$, NH(aryl-($C_5$–$C_{10}$)), NHCO-alkyl-($C_1$–$C_4$), NHCO-aryl-($C_5$–$C_{10}$), wherein, for the residues R$^1$ to R$^4$, alkyl represents a linear or branched, aliphatic or carbocyclic residue, alkenyl an olefinic hydrocarbon, alkynyl an acetylene hydrocarbon and aryl an aromatic residue. One to four carbon atoms of the carbocyclic and aromatic residue here can be replaced by one to four heteroatoms from the group of nitrogen, oxygen and sulfur atoms.

Alkyl, alkenyl, alkynyl, aryl, heterocycloalkyl and heteroaryl can preferably carry substituents which, independently of one another, signify hydrogen, ($C_2$–$C_{12}$)-alkyl, ($C_2$–$C_{12}$)-alkenyl, ($C_1$–$C_{10}$)-haloalkyl, ($C_3$–$C_8$)-cycloalkyl, ($C_5$–$C_8$)-cycloalkenyl, ($C_2$–$C_9$)-heterocycloalkyl, ($C_1$–$C_9$)-heterocycloalkenyl, ($C_5$–$C_{10}$)-aryl, ($C_2$–$C_{10}$)-heteroaryl, wherein the number of heteroatoms, preferably from the group N, O, S, can be one to four, fluorine, chlorine, bromine, iodine, OH, NO$_2$, CF$_3$, O-alkyl-($C_1$–$C_8$), O-aryl-($C_5$–$C_{10}$), OCO-alkyl-($C_1$–$C_8$), OCO-aryl-($C_5$–$C_{10}$), NH$_2$, NH(alkyl-($C_1$–$C_8$)), NH(aryl-($C_5$–$C_{10}$)), N(alkyl-($C_1$–$C_8$))$_2$, N(aryl-($C_5$–$C_{10}$))$_2$, NHCO-alkyl-($C_1$–$C_8$), NHCO-aryl-($C_5$–$C_{10}$), CH(O-alkene-($C_2$–$C_6$)—O), C(O-alkene-($C_2$–$C_6$)—O)-alkyl-($C_1$–$C_8$), C(O-alkene-($C_2$–$C_6$)—O)-aryl-($C_5$–$C_{10}$), CH(O-alkyl-($C_1$–$C_8$))$_2$, C(O-alkyl-($C_1$–$C_8$))$_2$-alkyl-($C_1$–$C_8$), C(O-alkyl-($C_1$–$C_8$))$_2$-aryl-($C_5$–$C_{10}$), CHO, CO-alkyl-($C_1$–$C_8$), CO-aryl-($C_5$–$C_{10}$), CN, COOH, COOM, COO-alkyl-($C_1$–$C_8$), C(=N-alkyl-($C_1$–$C_8$))O-alkyl-($C_1$–$C_8$), C(=N-aryl-($C_5$–$C_{10}$))O-alkyl-($C_1$–$C_8$), C(=N-alkyl-($C_1$–$C_8$))O-aryl-($C_5$–$C_{10}$), C(=N-aryl-($C_5$–$C_{10}$))O-aryl-($C_5$–$C_{10}$), CONH$_2$, CO-alkyl-($C_1$–$C_8$), NHCOH, NHCOO-alkyl-($C_1$–$C_4$), CO-aryl-($C_5$–$C_{10}$), COO-aryl-($C_5$–$C_{10}$), CHCH—COO-alkyl-($C_1$–$C_8$), CN, COOH, COOM, CHCHCO$_2$H, P(aryl-($C_5$–$C_{10}$))$_2$, P(alkyl-($C_1$–$C_8$))$_2$, PO(aryl-($C_5$–$C_{10}$))$_2$, PO(alkyl-($C_1$–$C_4$))$_2$, PO$_3$H$_2$, PO(alkyl-($C_1$–$C_4$))(O-alkyl-($C_1$–$C_6$)), PO(O-alkyl-($C_1$–$C_6$))$_2$, OPO(aryl)$_2$—($C_5$–$C_{10}$), OPO(alkyl)$_2$—($C_1$–$C_4$), OPOH(alkyl-($C_1$–$C_6$)), OPO$_3$H$_2$, OPO$_3$M$_2$, OPO(alkyl-($C_1$–$C_4$))(O-alkyl-($C_1$–$C_6$)), OPO (aryl-($C_5$–$C_{10}$))(O-alkyl-($C_1$–$C_6$)), OPO(O-alkyl-($C_1$–$C_6$))$_2$, OPO(O-aryl-($C_5$–$C_{10}$))$_2$, SO$_3$H, SO$_3$M, SO$_2$—O-alkyl-($C_1$–$C_4$), SO$_2$—O-aryl-($C_5$–$C_{10}$), SO$_2$-alkyl-($C_1$–$C_6$), SO$_2$-aryl-($C_5$–$C_{10}$), SO-alkyl-($C_1$–$C_6$)), SO-aryl-($C_5$–$C_{10}$), OSO$_3$H, OSO$_3$M, OSO$_2$—O-alkyl-($C_1$–$C_4$), OSO$_2$-alkyl-($C_1$–$C_6$) or Si(alkyl-($C_1$–$C_8$))$_3$, Si($C_{1–C8}$-alkyl/$C_5$–$C_{10}$-aryl)$_3$, wherein M represents a cation from the group Li$^+$, Na$^+$, K$^+$, Mg$^{2+}$, Ca$^{2+}$, NH$_4^+$, N($C_1$–$C_{10}$-alkyl)$_4^+$, N(H/$C_1$–$C_{10}$-alkyl/$C_6$–$C_{10}$-aryl)$_4^+$.

Particularly preferred are carbonyl compounds (II), in which residues R$^1$ and R$^2$ are different and thus an enantiomerically pure or enantiomer-enriched amine (III) can be synthesised.

The substituents from the aryl groups can also be π-bonded metal complexes of the general formulae (IV–V),

(IV)

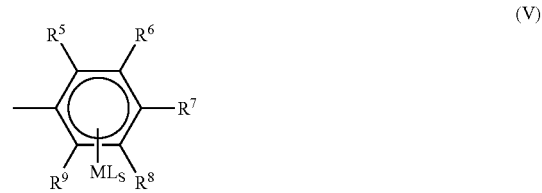

(V)

wherein s denotes whole numbers in the range of 1 to 6 and M denotes chromium, molybdenum, tungsten, manganese, rhenium, iron, cobalt, nickel or an element from the lanthanides series and R$^5$ to R$^9$ are the same or different and correspond to one of the residues defined for R$^3$–R$^4$ and wherein the ligands L$_1$ to L$_s$ are the same or different and denote a cyclic ether with 5–6 ring atoms, a cyclic olefin with 5–8 ring atoms, pyridine, CO, PF$_3$ or a ligand of the general formulae (VI) and (VII).

The reaction of the ketones or aldehydes to form amines according to the invention is achieved surprisingly efficiently by a reductive hydride transfer amination of the carbonyl compound in the presence of transition metal complexes with a catalytic action containing at least one metal from the group Fe, Ru, Os, Co, Rh, Ir, Ni, Pd, Pt and at least one mono- or bidentate nitrogen donor ligand, phosphorus donor ligand, cyclopentadienyl ligand, arene ligand, olefin ligand, alkyne ligand, heterocycloalkyl ligand, heteroaryl ligand, hydride ligand, alkyl ligand and/or carbonyl ligand.

In principle, all ligands that enter into stable complex compounds with metals from the eighth subgroup are suitable.

Examples of particularly suitable nitrogen, phosphorus, cyclopentadienyl and arene ligands are mono- or bidentate ligands of formula (VI) or (VII),

(VI)

(VII)

wherein L$^1$ and L$^2$, independently of one another, denote a coordinating group of formulae (VIII)–(XII)

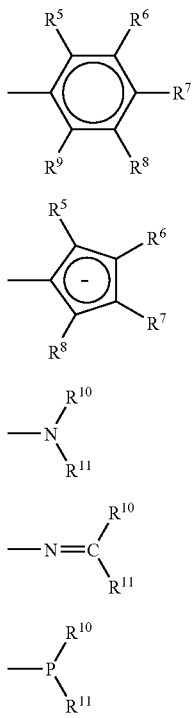

(VIII)

(IX)

(X)

(XI)

(XII)

wherein $R^5$ to $R^9$, independently of one another, are selected from the group hydrogen, $(C_1-C_{24})$-alkyl, $(C_2-C_{24})$-alkenyl, $(C_2-C_{24})$-alkynyl, $(C_5-C_{10})$-aryl, $CF_3$, CO-alkyl-$(C_1-C_8)$, CO-aryl-$(C_5-C_{10})$, CN, COOH, COOM, COO-alkyl-$(C_1-C_8)$, COO-aryl-$(C_5-C_{10})$, C(=N-alkyl-$(C_1-C_8)$)O-alkyl-$(C_1-C_8)$, C(=N-aryl-$(C_5-C_{10})$)(O-alkyl-$(C_1-C_8)$), C(=N-alkyl-$(C_1-C_8)$)(O-aryl-$(C_5-C_{10})$), C(=N-aryl-$(C_5-C_{10})$)(O-aryl-$(C_5-C_{10})$), $CONH_2$, CONH-alkyl-$(C_1-C_8)$, CON(alkyl-$(C_1-C_8)$)$_2$, CONH-aryl-$(C_5-C_{10})$, CON(aryl-$(C_5-C_{10})$)$_2$, PO(aryl-$(C_5-C_{10})$)$_2$, PO(alkyl-$(C_1-C_4)$)$_2$, POH(alkyl-$(C_1-C_6)$), POH(aryl-$(C_5-C_{10})$), PO(alkyl-$(C_1-C_4)$)(O-alkyl-$(C_1-C_6)$), PO(alkyl-$(C_1-C_6)$)(O-aryl-$(C_5-C_{10})$), PO(aryl-$(C_5-C_{10})$)(O-alkyl-$(C_1-C_6)$), $PO_3H_2$, $PO_3M_2$, PO(O-alkyl-$(C_1-C_6)$)$_2$, PO(O-aryl-$(C_5-C_{10})$)$_2$, PO(O-alkyl-$(C_1-C_6)$)(O-aryl-$(C_5-C_{10})$), $SO_3H$, $SO_3M$, $SO_3$-alkyl-$(C_1-C_4)$, $SO_3$-aryl-$(C_5-C_{10})$, $SO_2$-alkyl-$(C_1-C_6)$, $SO_2$-aryl-$(C_5-C_{10})$, SO-alkyl-$(C_1-C_8)$, SO-aryl-$(C_5-C_{10})$, S-alkyl-$(C_1-C_8)$, S-aryl-$(C_5-C_{10})$, SH, Si(alkyl-$(C_1-C_8)$)$_3$, Si($C_1-C_{10}$-alkyl/$C_5-C_{10}$-aryl)$_3$, $NO_2$, F, Cl, Br, I, O-alkyl-$(C_1-C_8)$, O-aryl-$(C_5-C_{10})$, OH, $NH_2$, NH(alkyl-$(C_1-C_8)$), N(alkyl-$(C_1-C_8)$)$_2$, NH(aryl-$(C_5-C_{10})$), NHCO-alkyl-$(C_1-C_4)$, NHCO-aryl-$(C_5-C_{10})$, NHCOO-alkyl-$(C_1-C_4)$, NHCOO-aryl-$(C_5-C_{10})$, OCO-alkyl-$(C_1-C_8)$, OCO-aryl-$(C_5-C_{10})$, OPO(aryl-$(C_5-C_{10})$)$_2$, OPO (alkyl-$(C_1-C_4)$)$_2$, OPOH(alkyl-$(C_1-C_6)$), $OPO_3H_2$, $OPO_3M_2$, OPO-alkyl-$(C_1-C_4)$(O-alkyl-$(C_1-C_6)$), OPO(O-alkyl-$(C_1-C_6)$)$_2$, OPO(O-aryl-$(C_5-C_{10})$)$_2$, $OSO_3H$, $OSO_3M$, $OSO_2$—$CF_3$, $OSO_3$-alkyl-$(C_1-C_4)$, $OSO_3$-aryl-$(C_5-C_{10})$, $OSO_2$-alkyl-$(C_1-C_6)$, $OSO_2$-aryl-$(C_5-C_{10})$, wherein M represents a cation $Li^+$, $Na^+$, $K^+$, $Mg^+$, $Ca^+$, $NH_4^+$, $N(C_1-C_{10}$-alkyl)$_4^+$, $N(C_1-C_{10}$-alkyl/$C_5-C_{10}$-aryl)$_4^+$, and wherein the residues $R^{10}$ to $R^{12}$, independently of one another, can represent a hydrogen, $(C_1-C_{24})$-alkyl, $(C_2-C_{24})$-alkenyl, $(C_2-C_{24})$-alkynyl, $C_5-C_8$ cycloalkenyl, $(C_5-C_{14})$-aryl, O-alkyl-$(C_1-C_8)$, O-aryl-$(C_5-C_{14})$, O-alk-enyl-$(C_2-C_{24})$, O-alkynyl-$(C_2-C_{24})$, O-cycloalkenyl-$(C_5-C_8)$, o-aryl-$(C_5-C_{14})$, F, $NH_2$, NH(alkyl-$(C_1-C_8)$), NH-alkenyl-$(C_2-C_{24})$, NH-alkynyl-$(C_2-C_{24})$, NH-cycloalkenyl-$(C_5-C_8)$, NH-aryl-$(C_5-C_{14})$, N(alkyl-$(C_1-C_8)$)$_2$, N(alkenyl-$(C_2-C_{24})$)$_2$, N(alkynyl-$(C_2-C_{24})$)$_2$, N(cycloalkenyl-$(C_5-C_8)$)$_2$, N(alkyl-$(C_1-C_8)$)(aryl-$(C_5-C_{10})$), N(aryl-$(C_5-C_{10})$)$_2$, NHCO-alkyl-$(C_1-C_4)$, NHCO-alkenyl-$(C_2-C_{24})$, NHCO-alkynyl-$(C_2-C_{24})$, NHCO-cycloalkenyl-$(C_5-C_8)$, NHCO-aryl-$(C_5-C_{14})$; OCO-alkyl-$(C_1-C_4)$, OCO-alkenyl-$(C_2-C_{24})$, OCO-cycloalkenyl-$(C_5-C_8)$, OCO-aryl-$(C_5-C_{14})$, $SO_2$-alkyl-$(C_1-C_6)$, $SO_2$-aryl-$(C_5-C_{10})$ residue and in which all the above-mentioned substituents can each be mono-or polysubstituted, the cyclic aliphatic or aromatic residues preferably being 5- to 7-membered rings, wherein optionally two adjacent residues together can also denote saturated or unsaturated carbocyclic or heterocyclic groups having 3 to 15 atoms, with one to four nitrogen, phosphorus, silicon, sulfur or oxygen atoms. Substituents from the cyclopentadienyl and aryl groups can also mean π-bonded metal complexes of the general formulae (IV) or (V).

Q represents a bridge linking the unit $L^1$ with the unit $L^2$ of the formula (XIII):

$$X^1-Z-X^2 \qquad (XIII)$$

wherein $X^1$ and $X^2$, independently of one another, represent a direct bond or a group
—O—, —S—, or —$NR^{13}$—, wherein $R^{13}$ can be one of the residues defined for $R^{10}-R^{12}$ and wherein
Z can be a direct bond or can consist of 1–16 carbon atoms linked by single or multiple bonds, wherein one to four carbon atoms can be replaced by heteroatoms, preferably from the group N, O, S or Si, so that e.g. an aliphatic, heteroaliphatic, cycloaliphatic, heterocycloaliphatic, olefinic, heteroolefinic, acetylenic, heteroacetylenic, cycloolefinic, heterocycloolefinic, aromatic or heteroaromatic system or a metallocene is present, which can be mono- or polysubstituted with substituents as stated for $R^5-R^9$ or can carry a keto (=O), thioketo (=S) or imide substituent (=$NR^{14}$), wherein $R^{14}$ can be one of the residues defined for $R^{10}-R^{12}$ and wherein the units $L^1$ and $R^{12}$ or $L^1$ and Q or $L^2$ and Q can be linked together in such a way that a saturated or unsaturated carbocyclic skeleton having 3 to 15 atoms or a saturated or unsaturated, heterocyclic skeleton containing one to four nitrogen, phosphorus, silicon, sulfur or oxygen atoms is formed.

In a preferred embodiment, Q in formula (VII) represents an aliphatic, olefinic or acetylenic bridge consisting of one to fourteen carbon atoms, wherein one to four carbon atoms can be replaced with nitrogen or silicon atoms or one to two carbon atoms can be replaced with oxygen or sulfur atoms and wherein the individual binding links of the group, independently of one another, can carry substituents as defined for $R^5-R^9$ or a keto (=O), thioketo (=S) or imide substituent (=$NR^{14}$), wherein $R^{14}$ can be one of the residues defined for $R^{10}-R^{12}$ and wherein two of the units $L^1$, $L^2$ and Q can be linked together so that a saturated or unsaturated carbocyclic skeleton having 5 to 9 atoms or a saturated or unsaturated heterocyclic skeleton containing one to four nitrogen, phosphorus, silicon, sulfur or oxygen atoms is formed.

Examples of olefin and alkyne ligands are mono-, bi-, tri- or tetradentate, linear, branched or polycyclic, particularly mono- and bicyclic, alkynes, olefins, conjugated or non-conjugated di- tri- or tetraenes with two to twelve carbon atoms, wherein one to four carbon atoms can be replaced with nitrogen or silicon atoms or one to two carbon atoms can be replaced with oxygen or sulfur atoms and wherein the individual members of the group, independently of one another, can carry substituents as defined for $R^5$–$R^9$ or a keto (=O), thioketo (=S) or imide substituent (=$NR^{14}$), wherein $R^{14}$ can be one of the residues defined for $R^{10}$–$R^{12}$.

Examples of heterocycloalkyl or heteroaryl ligands are mono- or bidentate polycyclic, particularly mono- and bicyclic together for saturated or unsaturated heterocyclic ligands having 3 to 15 atoms, with one to four oxygen, sulfur or nitrogen atoms, or ($C_3$–$C_{13}$) heteroaromatics, with one to four oxygen, sulfur, nitrogen or one to two phosphorus atoms, wherein the individual binding links, independently of one another, can carry substituents as defined for $R^5$–$R^9$ or a keto (=O), thioketo (=S) or imide substituent (=$NR^{14}$), wherein $R^{14}$ can be one of the residues defined for $R^{10}$–$R^{12}$.

Preferred ligands are ligands of the general formulae (VI) and (VII), among which, in turn, those preferred are the ones in which $R^5$ to $R^{12}$, independently of one another, are $C_1$–$C_8$-alkyl, $C_5$–$C_6$-cycloalkyl, $C_6$-aryl, $C_4$–$C_5$-heteroaryl, wherein the number of heteroatoms is 1–2, preferably selected from the group N, O, S and the ring size is 5–6, naphthyl, O-alkyl-($C_1$–$C_8$), O-aryl-$C_6$, O-cycloalkenyl-($C_5$–$C_8$), O-aryl-$C_6$, O-phenyl, O-naphthyl, F, $NH_2$, NH(alkyl-($C_1$–$C_8$)), NH-cycloalkenyl-($C_5$–$C_8$), NH-phenyl, NH-naphthyl, N(alkyl-($C_1$–$C_8$))$_2$, N(cycloalkenyl-($C_5$–$C_8$))$_2$, N(alkyl-($C_1$–$C_8$))(aryl-$C_6$), N(aryl-$C_6$)$_2$, these groups and coordinating cyclopentadienyl and aryl groups of the general formulae (VIII–IX) optionally carrying one or more substituents, with preferred substituents being those which, independently of one another, can be hydrogen, $C_1$–$C_{10}$ alkyl, $C_1$–$C_6$ haloalkyl, $C_5$–$C_6$ cycloalkyl, $C_2$-$C_8$ heterocycloalkyl, phenyl, $C_4$–$C_5$ heteroaryl, wherein the number of heteroatoms, preferably from the group N, O, S, can be 1–2, $C_1$–$C_6$ alkoxy, OCO-alkyl-($C_1$–$C_6$), O-aryl-$C_6$, trihalomethyl, fluoro, chloro, bromo, iodo, nitro, hydroxy, oxo, thio, thiolato, amino, $C_1$–$C_8$ substituted amino of the forms mono-, di-, tri- $C_1$–$C_8$-alkylamino or $C_2$–$C_8$ alkenylamino or mono- and di-$C_6$–$C_8$ arylamino or $C_1$–$C_8$-alkyl-$C_6$–$C_8$-arylamino, NH—CO-alkyl-$C_1$–$C_8$, NH—CO-aryl-$C_6$–$C_8$, $C_1$–$C_8$-acyloxy, carboxyl, carboxylato of the form $COOR^{14}$, sulfinato, sulfonato of the form $SO_3R^{14}$, phosphonato of the form $PO_3H_2$, $PO_3HR^{14}$, $PO_3R^{14}{}_2$, wherein $R^{14}$ represents either a mono- or divalent cation ($Li^+$, $Na^+$, $K^+$, $Mg^{2+}$, $Ca^{2+}$), $NH_4{}^+$, $N(C_1$–$C_{10}$-alkyl)$_4{}^+$, $N(H/C_1$–$C_{10}$-alkyl/$C_6$–$C_{10}$-aryl)$_4{}^+$, $C_1$–$C_8$-alkyl or $C_6$-aryl, tri-$C_1$–$C_6$ alkylsilyl.

Also preferred are ligands in which Q consists of one to four carbon atoms and an oxygen or nitrogen atom, particularly preferably of two carbon atoms. If Q is part of a cyclic structural element, three- to nine-membered ring systems are preferred. Five- to seven-membered ring systems are particularly preferred. The ring system can contain one to four heteroatoms, preferably one to two. Preferred heteroatoms are O, N and S. The nitrogen of the ring system can be present as $NR^{13}$, $NR^{13}R^{13+}$, $NR^{13}H^+$, $NC(O)R^{13}$. The ring systems can be directly mono- or polysubstituted as stated for $R^5$ to $R^9$, and the substituents can also be bridged to one another.

Particularly preferred ring systems are phenyl, ferrocenyl, cyclopentyl, cyclohexyl, pyridyl, pyrrole, furyl, thiophene, tetrahydrofuran, tetrahydrothiophene, piperidyl, pyrrolidinyl, dioxolane or sulfolane rings, unsubstituted or substituted as stated above.

Metallocenes such as ferrocenes and arene complexes such as benzene chromium tricarbonyl are included in the group of the aromatics within the meaning of this invention.

Examples of particularly suitable achiral or chiral ligands are represented by compounds of the formulae:

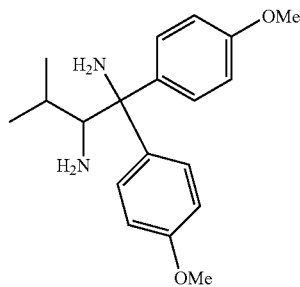

DAIPEN

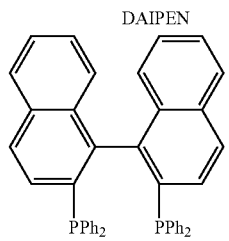

BINAP

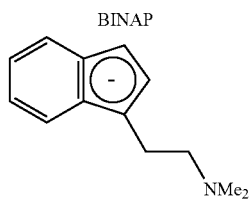

Dmaelnd

Other chiral and achiral phosphane and diphosphane ligands that can preferably be used are e.g. dppb (1,4-bis(diphenylphosphino)butane), dcypb (1,4-bis(dicyclohexylphosphino)butane), (R,R)-DIPAMP ((1R,2R) -bis [(2-methoxyphenyl) phenylphosphino]ethane); (R)-Norphos ((2R,3R)-(−)-2,3-bis(diphenylphosphino)-bicyclo[2.2.1]hept-5-ene); (R,R)-CHIRAPHOS ((2R,3R)-(−)bis(diphenyl-phosphino) butane) (S. H. Bergens, J. Whelan, B. Bosnich Inorg. Synth. (1997), 31, 131–138); (R,R)-DEGUPHOS ((3R,4R)-(+)-1-benzyl-3,4-bis(diphenylphosphino)-pyrrolidine); (R)-CyGanterPhos ((R)-[3,4-dimethylphosphaferrocen-2-yl)methyl] dicyclohexylphosphane); (R,R)-Me-DUPHOS ((−)-1,2-bis ((2R,5R)-2,5-dimethylpholano)benzene); (R,R)-Et-DUPHOS ((−)-1,2-bis((2R,5R)-2,5-diethylpholano) benzene); (R,R)-Me-BPE ((+)-1,2-bis((2R,5R)-2,5-dimethylpholano)ethane); (R,R)-Et-BPE ((+)-1,2-bis ((2R,5R)-2,5-diethylpholano)ethane); (R)-bis (MePheP)benzene ((1R,2R)-(+)-bis (methylphenylphosphino)benzene); (R)-PROPHOS (2-(R)-1,2-bis(diphenylphosphino)propane); (R,R)-SKEWPHOS ((2R,4R)-(−)bis(diphenylphosphino)pentane) (P. A. MacNeil, N. K. Roberts, B. Bosnich J. Am. Chem. Soc. (1981), 103, 2273–80); (S)-Phos4 ((S)-1-[2'-(diphenylphosphino)-phenyl]diphenylphosphinoethane; (R,S)-Cy-Fc-etdpp ((R)-1-{(1S)-2-(dicyclohexylphosphino) ferrocenyl}ethyldiphenylphosphine; (R,S)-Cy-Fc-etdCyP ((R)-1-{(1S)-2-(dicyclohexylphosphino)ferrocenyl}ethyldicyclohexylphosphin e); (R,S)-Ph-Fc-etdt-BuP ((R)-1-{(1S)-2-(diphenylphosphino)ferrocenyl}ethyldi-tert-butylphosphine); (R,S)-JOSIPHOS ((R)-1-{(1S)-2-(diphenylphosphino)ferrocenyl}ethyldicyclohexylphosphine) (EP 564406); (R)-carboxybutyl-BINAP ((R)-(+)-7-carboxybutyl-2,2'-bis(diphenylphosphino)-1,1'-binaphthyl); (R)-BINAP ((R)-2,2'-bis(diphenylphosphino)-1,1'-binaphthyl) (A. Miyashita, A. Yasuda, H. Takaya, K. Toriumi, T. Ito, T. Souchi, R. Noyori, R. J. *Am. Chem. Soc.* (1980), 102, 7932–4); (R)-Tol-BINAP ((R)-2,2'-bis(di-p-tolylphosphino)-1,1'-binaphthyl) (H. Takaya, K. Mashima, K. Koyano, M. Yagi, H. Kumobayashi, T. Taketomi, S. Akutagawa, R Noyori *J. Org. Chem.* (1986), 51, 629–35); (R)-MeO-BIPHEP ((R)-(−)-2,2'-bis(diphenylphosphino)-6,6'-dimethoxy-1,1'-biphenyl); (R)-p-Tol-MeO-BIPHEP ((R)-(−)-2,2'-bis(di-p-tolylphosphino)-6,6'-dimethoxy-1,1'-biphenyl); (S,S)-1,2-(BDPPm-ethyl)-cyclohexane ((1S,2S)-(+)-trans-1,2-bis(diphenylphosphinomethyl)cyclohexane); (S,S)-DIOP (4S,5S—(+)-1,4-bis(diphenylphosphino)-1,4-dideoxy-2,3-isopropylidene-D-threitol) (Kagan et al. *J. Amer. Chem. Soc.* (1972), 94, 6429); (S)-MOD-DIOP(S,S-(+)-1,4-bis[bis(3,5-dimethyl-4-methoxyphenylphosphino)]-1,4-dideoxy-2,3-isopropylidene-D-threitol); (R)-MeAAPHOS ((2R,3R,5R,6R)-2,3-dimethoxy-2,3-dimethyl-5,6-bis(diphenylphosphinomethyl)-1,4-dioxane) (Berens et al. *J. Org. Chem.* (1995), 60, 8204), (S,S)-BPPM-H ((2S,4S)-(−)-4-diphenylphosphino-2-(diphenylphosphinomethyl)pyrrolidine); (S,S)-BPPM ((2S,4S)-N-tert-butoxycarbonyl-4-(diphenylphosphino)-2-(diphenylphosphinomethyl)pyrrolidine) (I. Ojima, T. Kogure, N. Yoda *J. Org. Chem.* (1980), 45, 4728-39); (R,R)-phenyl-CAPP ((2R,4R)-N-anilidooxy-4-(diphenylphosphino)-2-(diphenylphosphinomethyl)pyrrolidine); (R)-NAPHOS ((R)-(+)-2,2'-bis(diphenylphosphinomethyl)-1,1'-binaphthyl); diphosphonite ligands based on carbohydrate, such as e.g. Ph-β-Glup (phenyl 4,6-O-benzylidene-2,3-bis(O-diphenylphosphino)-p-D-glucopyranoside) or Ph-p-Glup-OH (phenyl 2,3-bis(O-diphenylphosphino)-β-D-glucopyranoside) described in DD 140036 and WO 95/18787 and related ligand systems such as e.g. DPOE (1,2-bis(diphenylphosphinoxy)ethane) (S. Bolano, J. Bravo, R. Carballo, S. Garcia-Fontan, U. Abram, E. M. Vazquez-Lopez *Polyhedron* (1999), 18, 1431–1436); (R,R)-bdpch ((1R,2R)-(trans)-1,2-bis(diphenylphosphinoxy)cyclohexane) (M. Tanaka, I. Ogata *J. Chem. Soc., Chem. Commun.* (1975), 735); (R,R)-CYLOPP-2-Me ((1R,2R)-(trans)-1,2-bis(di-(2-methylphenyl)phosphinoxy)cyclohexane); (R,R)-CYCLOPP-4-CF3 ((1R,2R)-(trans)-1,2-bis(di-(4-trifluoromethylphenyl)phosphinoxy)cyclohexane); (R,R)-CYCLOPP-3,5-Cl ((1R,2R)-(trans)-1,2-bis(di-(3,5-dichlorophenyl)phosphinoxy)cyclohexane); (R,R)-CYCLOPP-3,5-CF3 ((1R,2R)-(trans)-1,2-bis(di-(3,5-bis-trifluoromethyl)phenyl)phosphinoxy)cyclohexane); (R,R)-CYCLOPP-3,5-F ((1R,2R)-(trans)-1,2-bis(di-(3,5-difluorophenyl)phosphinoxy)cyclohexane); CARBOPHOS-3,5-Me2Ph (methyl 2,6-(O)-dibenzoyl-3,4-(O)-bis(bis(3,5-dimethylphenyl)phosphino)-α-D-glucopyranoside); GLUCOPHOS-Ph-3,5-Me (phenyl-4,6-O-(R)-benzylidene-2,3-(O)-bis(bis(3,5-dimethylphenyl)phosphino)-p-D-glucopyranoside); R-POP-Bz ((3R,4R)-3,4-diphenylphosphinoxy-1-benzylpyrrolidine) (M. Yatagai, T. Yamagishi, M. Hida *Bull. Chem. Soc. Jpn.* (1984), 57, 823–6); (R,S)-Phos3 ((3R,4S)-3-diphenylphosphinoxy-4-[4-(di(4-fluorophenyl)phosphino-2,5-dimethyl-3-thienyl]tetrahydrofuran) and aminophosphine phosphinites (Agbossou et al., Coordination Chemistry Rev. 1998, 178–180, 1615), such as e.g. (S)-CyCy-OxoPRONOP ((S)-1-(dicyclohexylphosphino)-2-(dicyclohexylphosphinoxymethyl)-pyrrolidone-5); (S)-Cy,Cy-PRONOP ((S)-1-(dicyclohexylphosphino)-2-(dicyclohexylphosphinoxymethyl)pyrrolidine); (S)-CyCyisoALANOP ((S)-2-(N-methyl-N-dicyclohexylphosphino)amino-1-(dicyclohexylphosphinoxy)propane); (R)-PROPRAPHOS ((R)-2-(N-isopropyl-N-diphenylphosphino)amino-1-(diphenylphosphinoxy)propane) and PROPRAHOS analogue (R)-Cyp-PPP ((2R)-1-[[(diphenylphosphino)(cyclopentyl)amino]-methyl]-2-diphenylphosphinoxy-3-(1-naphthalenyloxy)propane) (Krause et al. *J. Mol. Catal. A: Chem.* (1995), 104, 147), aminophosphanes, such as e.g.: (R)—PN-Ph ((R)-(−)-2-[2-(diphenylphosphino)-phenyl]-4-phenyl-1,3-oxazoline); (S)-PN-iPr ((S)-(+)-2-[2-(diphenylphosphino)-phenyl]-4-isopropyl-1,3-oxazoline); (S)—PN-iPr-Me ((S)-(+)-2-[2-(diphenylphosphino)-phenyl]-4-(isopropyl)-methyl-1,3-oxazoline); (S)-PN-tBu ((S)-(+)-2-[2-(diphenylphosphino)-phenyl]-4-(2-methyl)-isopropyl-1,3-oxazoline) (Koch G., Lloyd-Jones G. C., Loiseleur O., Pfaltz A., Pretot R., Schaffner S., Schnider P., von Matt P. Recl. Trav. Chim. Pays-Bas 1995, 114, 206-10); (R)-QUINAP ((R)-(+)-1-(2-diphenylphosphino-1-naphthyl)-isoquinoline); (R,R)-(S,S)-EtTRAP ((R,R)-2,2"-bis[(S)-1-(diethylphosphino)ethyl]-1,1"-bisferrocene). The phosphorus-containing ligands can be produced by synthetic processes known to the person skilled in the art, e.g. by methods as described in Chemistry of Organophosphorus Compounds, ed. F. R. Hartley, serial ed. S. Patai, vol. 1, John Whiley, 1990. Some of the ligands and metal complexes are also commercially available.

In addition to the preferred ligands, mono- or bidentate, linear, branched or cyclic, particularly mono- and bicyclic, olefinic ligands or alkynes with two to twelve carbon atoms or ($C_3$–$C_{13}$) heteroaromatics with one to four nitrogen or one to two phosphorus atoms are also suitable. Examples of olefinic ligands are ethylene, butadiene, cyclohexene, 1,3-cyclohexadiene, cis-cyclooctene, 1,5-cis,cis-cyclooctadiene, norbornene, norbornadiene. Examples of heteroaromatics are pyridine, 2,2'-bipyridyl, phosphabenzene and phosphaferrocene.

The production of the catalytically active metal-ligand complex compounds can take place in situ by the reaction of a metal salt or an appropriate pre-complex with the ligands of the general formulae (VI) and/or (VII). In addition, a metal-ligand complex compound can be obtained by reaction of a metal salt or an appropriate pre-complex with the ligands of the general formula (VI) and/or (VII) and subsequent isolation.

The metal complexes can be synthesised, for example, in that, by a known method (EP-A-0158875; EP-A-0437690), e.g. by reaction with iron, rhodium, osmium, iridium, ruthenium, palladium, platinum, cobalt or nickel complexes, which contain unstable ligands (e.g. [Rh(COD)$_2$]BF$_4$, [RuCl$_2$(C$_6$H$_6$)]$_2$, [RuCl$_2$(C$_5$Me$_5$)]$_2$, [Ir(COD)Cl]$_2$), with the achiral or chiral ligands of the general formulae (VI) and/or (VII) catalytically active complexes are generated. Other processes for the production of metal complexes are described in Comprehensive Organometallic Chemistry II, Pergamon 1995. The catalysts can be produced immediately before reaction from the metal precursor and the ligands of formula (VI) and/or (VII) in situ or in an inert solvent, or they are used in isolated form. Many of the catalysts or ligands and pre-complexes that can be used are also commercially available.

Examples of metal salt educts that can be used are their chlorides, bromides, iodides, nitrates, acetates, acetylacetonates, hexafluoroacetylacetonates, perfluoroacetates or triflates.

Examples of suitable pre-complexes are: bis(cyclooctene) rhodium(I) chloride dimer, 1,5-cyclooctadienerhodium(I) chloride dimer, norbornadienerhodium(I) chloride dimer, 1,5-hexadienerhodium(I) chloride dimer, tris(triphenylphosphane)rhodium(I) chloride, hydridocarbonyltris(triphenylphosphane)rhodium(I) chloride, bis(1,5-cyclooctadiene)rhodium(I) perchlorate, bis(1,5-cyclooctadiene)rhodium(I) tetrafluoroborate, bis(1,5-cyclooctadiene)rhodium(I) triflate, bis(acetonitrile)(1,5-cyclooctadiene)rhodium(I) perchlorate, bis(acetonitrile)(1,5-cyclooctadiene)rhodium(I) tetrafluoroborate, bis(acetonitrile)(1,5-cyclooctadiene)rhodium(I) triflate, cyclopentadienylrhodium(III) chloride dimer, pentamethylcyclopentadienylrhodium(III) chloride dimer, cyclooctadieneiridium(I) chloride dimer, bis(cyclooctene)iridium(I) chloride dimer, bis(2,2,6,6-tetramethyl-3,5-heptanedionato)(1,5-cyclooctadiene)ruthenium (II), carbonyl(dihydrido)tris(triphenylphosphine)ruthenium (II), chloro(cyclopentadienyl)bis(triphenylphosphine)ruthenium (II), chloro(indenyl)bis(triphenylphosphine)ruthenium (II), cis-dichlorobis(2,2'-bipyridine)ruthenium (II) dihydrate, dichloro(1,5-cyclooctadiene)ruthenium (II), dichlorodicarbonylbis(triphenylphosphine)ruthenium (II), dichloro(pentamethylcyclopentadienyl)ruthenium (III), dichlorotris(triphenylphosphine)ruthenium (II), tris(2,2'-bipyridyl)ruthenium (II) chloride, benzeneruthenium(II) chloride dimer, dichloro(p-cymene)ruthenium(II) dimer, (bicyclo[2.2.1]hepta-2,5-diene)dichlororuthenium(II), bis(2-methylallyl)-1,5-cyclooctadiene-ruthenium.

In the reaction of the ligands of formulae (VI) and (VII) with the metal pre-complexes, e.g. complex compounds of type (XIV) can be obtained, which can act as catalysts in the reductive hydride transfer amination according to the invention,

$$[M_xL'_mL''_nS_q]Ar \qquad (XIV)$$

wherein, in the general formula (XIV), M represents a preferably mononuclear Fe, Ru, Os, Co, Rh, Ir, Ni, Pd or Pt metal centre, L" represents the same or different coordinating organic or inorganic ligands from the pre-complex and L' represents organic ligands of the formulae (VI) and/or (VII), S represents coordinating solvent molecules and A equivalents of non-coordinating anions, wherein x and m are integers greater than or equal to 1 and n, q and r are integers greater than or equal to 0.

The sum of m+n+q has its upper limit set by the coordination centres available at the metal centres, not all the coordination points having to be occupied.

Preferred ligands L" of these complex compounds are e.g. halide, particularly Cl, Br and I, diene, particularly cyclooctadiene, norbornadiene, olefin, particularly ethylene and cyclooctene, tri- and tetrahapto ligands, particularly 2-methylallyl, indenyl, pentamethylcyclopentadienyl and cyclopentadienyl anion, acetato, trifluoracetato, acetylacetonato and hexafluoroacetylacetonato, $PF_3$ as well as carbonyl and hydrido ligands.

Preferred coordinating solvents S are amines, particularly triethylamine and pyridine, alcohols, particularly methanol, ethers, particularly THF and dioxane, carboxylic acid amides, particularly DMF and aromatics, particularly benzene and cumene.

Preferred non-coordinating anions A are p-toluenesulfonate, methylsulfonate, trifluoromethylsulfonate, $BF_4$, $ClO_4$, $PF_6$, and $BAr_4$.

The catalysts can be produced immediately before or during the reaction from the metal precursor and the ligand in situ or in an inert solvent. However, they can also be produced in advance and optionally used in isolated form.

The catalyst is typically employed in quantities of 0.001 to 10 mole %, preferably 0.01 to 5 mole %, especially 0.1 to 1 mole %, based on the carbonyl component of formula (I).

The quantity of ligand is preferably in the range of 0.01 to 50 mole equivalents, preferably 0.5 to 5 mole equivalents, especially 1 to 2 mole equivalents, based on the quantity of metal precursor used.

The catalyst can also be employed in support-bound form, with aluminosilicates, silicon dioxides such as silica gels or kieselguhrs, activated carbon, aluminium oxides or zeolites being mentioned as support materials.

As hydrogen donors, primary and secondary alcohols, hydroaromatic and heterocyclic compounds, terpenes, N-benzylaniline, hydrazine, trialkylsilanes, trialkyltin hydrides, carboxylic acids and phosphinous acids and their esters, amides and ammonium salts and mixtures thereof are used.

The primary and secondary alcohols that can be employed as hydrogen donors are linear and branched, aliphatic, aliphatic-aromatic, cyclic alcohols or phenols, which each contain 1 to 20, preferably 1 to 6, particularly preferably 2 to 4 carbon atoms. Furthermore, carbohydrates and polyvinyl alcohols can also be used. Examples of alcohols are ethanol, ethylene glycol, propanol, isopropanol, butanol, isobutanol, 1,6-hexanediol, cyclopentanol, cyclohexanol, phenol, hydroquinone, benzyl alcohol, benzhydrol and glucose. Isopropanol is particularly preferred.

The hydroaromatic and heterocyclic compounds that can be used according to the invention as hydrogen donors are partially hydrogenated aromatics and heteroaromatics, as well as saturated, heterocyclic compounds. Examples of hydroaromatic and heterocyclic compounds are cyclohexene, cyclohexadiene, indane, Tetralin, dihydrofuran, pyrrolidine, piperidine, dioxane, indoline and tetrahydroquinoline.

The carboxylic acids that can be used as hydrogen donors according to the invention are linear or branched alkanecarboxylic acids which each contain 1 to 20, preferably 1 to 6 carbon atoms and optionally have one or more groups that can be selected from the group alkenyl, aryl, CO-alkyl-($C_1$–$C_{l0}$), CO-aryl-($C_6$–$C_{10}$), COOH, COO-alkyl-($C_1$–$C_{10}$) and OH. Examples of carboxylic acids are formic acid, ascorbic acid, lactic acid and phenylpyruvic acid.

Ester within the meaning of the present invention is formed from a carboxylic acid and ($C_1$–$C_{10}$) alcohol.

In a preferred embodiment, carboxylic acids are used as amine or ammonium salts, amine and ammonium cation denoting ammonia or an aromatic or non-aromatic, primary, secondary or tertiary amine and ammonium cation as well as a quaternary ammonium cation, each containing 1 to 20, preferably 1 to 6, carbon atoms. Examples of amines are trimethylamine, triethylamine, diisopropylethylamine and pyridine. Ammonium formate, triethylammonium formate and formic acid-triethylamine mixture are particularly preferred The process according to the invention for the hydride transfer reductive amination of carbonyl compounds is particularly preferably carried out with isopropanol, ammonium formate, triethylammonium formate or formic acid-triethylamine mixture as hydrogen donor. Hydrogen can also be employed as co-reductant.

It can be advantageous for the process according to the invention to work in the presence of additives. Additives are bases, such as sodium hydroxide solution, potassium hydroxide solution, tertiary amines, proton sponge, caesium carbonate, acetate, soda, salts such as the halides of the alkali metals or halides of ammonium salts, phase transfer catalysts, surfactants, cyclodextrins, which are employed from 0–100 mole %, based on the carbonyl component (I) used.

The hydride transfer amination is preferably performed in solution. Suitable as solvents are e.g. alcohols, especially $C_1$–$C_6$ alkanols, especially preferably methanol, ethanol, propanol, isopropanol, butanol or also water and mixtures thereof. In the case of sparingly soluble substrates, solvent mixtures of alcohols and halogenated hydrocarbons, such as chloroform and/or ethers, especially cyclic ethers such as THF, and/or hydrocarbons, such as hexane or toluene, are suitable. If catalyst is generated in a suitable solvent, catalyst solution is added to the reaction mixture.

The process according to the invention is generally carried out at a temperature of –78 to 150° C., preferably at –20 to 110° C., especially at 0 to 80° C. The reaction period is in the range of 30 min to 24 hours, depending on the substrate, amine and temperature.

EXPERIMENTAL

The following examples serve to explain the invention, without this being limited thereto.

Example 1

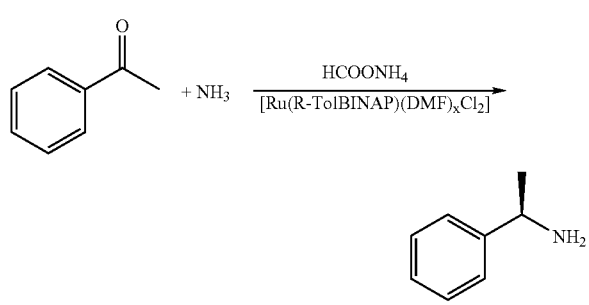

In a pressure vessel, 0.63 g of ammonium formate, 40 mg (0.04 mmol) of [Ru(R-TolBINAP) (DMF)$_x$Cl$_2$] and 4 ml of 20% ammonia solution were added to 240 mg (2 mmol) of acetophenone and stirred for 16 hours at 100° C. After cooling, the mixture was investigated by gas chromatography. Under these conditions, 4% of the ketone was reacted to 1-phenylethanol and 96% to (R)-1-phenylethylamine with an optical purity of 93% ee.

Examples 2–10

These examples are performed in the same way as Example 1. Catalysts and the reaction results are given in Table 1.

TABLE 1

| Catalyst | T (° C.) | Time (h) | Educt | 1-Phenylethylamine | ee (%)[e] | 1-Phenylethanol |
|---|---|---|---|---|---|---|
| 2 [Ru(R-TolBINAP)(R-DAIPEN)Cl$_2$][b] | 80 | 17 | 4 | 96 | 90(R) | |
| 3 [Ru(S-BINAP)(DMF)$_x$Cl$_2$] | 100 | 16 | 0 | 78 | 83(S) | 21 |
| 4 [Ru(PPh$_3$)$_3$Cl$_2$] | 80 | 7 | 72 | 17 | — | 10 |
| 5 [Ru(PPh$_3$)$_2$(C$_5$H$_5$)Cl] | 80 | 7 | 6 | 78 | — | 15 |
| 6 [Ir(C$_8$H$_{12}$)Cl]$_2$ | 80 | 12 | 15 | 84 | — | 1 |
| 7 [Ir(C$_8$H$_{12}$)Cl]$_2$ + Bpy[c] | 80 | 7 | 19 | 81 | — | 0 |
| 8 [Ir(C$_8$H$_{14}$)$_2$Cl]$_2$ + S-Norphos[d] | 80 | 24 | 0 | 63 | 23(R) | 36 |
| 9 [Ir(C$_8$H$_{14}$)$_2$Cl]$_2$ + R-TolBINAP | 80 | 24 | 14 | 73 | 0 | 12 |
| 10 [Rh(C$_5$Me$_5$)C$_2$I]$_2$ | 80 | 24 | 0 | 98 | — | 1 |

[a]Conditions: 2 mmol acetophenone, 10 mmol ammonium formate, 0.04 mmol pre-catalyst, 4 ml 20% ammonia solution in MeOH;
[b]R-DAIPEN = (2R)-(-)-1,1-bis(4-methoxyphenyl)-3-methyl-1,2-butanediamine;
[c]Bpy = 2,2'-bipyridyl;
[d]S-Norphos = (2S,3S)-(+)-2,3-bis(diphenylphosphino)-bicyclo[2.2.1]hept-5-ene;
[e]GC analysis of N-trifluoroacetyl derivative on a CP-Chirasil-Dex CB chiral column.

Example 11

51.5 mg (0.16 mmol) of [Ru(COD)(methallyl)$_2$] and 122 mg (0.18 mmol) of R-TolBINAP were dissolved in 8 ml of CH$_2$Cl$_2$ and 48 µl of tetrafluoroboric acid in Et2O were added, and then 1 ml (0.02 mmol) of catalyst solution was added to a solution of 240 mg (2 mmol) of acetophenone and 87 mg of formic acid-triethylamine complex (5:2) in 4 ml of 20% ammonia solution in MeOH and stirred for 12 hours at 60° C. in a pressure vessel. After cooling, the mixture was investigated by gas chromatography. Under these conditions, 49% of the ketone was reacted to (R)-1-phenylethylamine with an optical purity of 90% ee.

Examples 12–13

These examples are carried out in the same way as Example 11. Catalysts and the reaction results are given in Table 2.

TABLE 2[a]

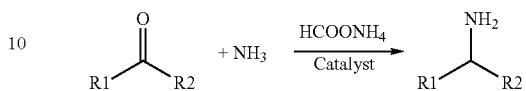

| Catalyst | T (° C.) | Time (h) | Educt | 1-Phenyl ethylamine | ee (%)[b] | 1-Phenyl ethanol |
|---|---|---|---|---|---|---|
| 12 | [Ru(S-BINAP) (DMF)$_x$Cl$_2$] | 70 | 38 | 4 | 48 | 80(S) | 47 |
| 13 | [Rh(C$_5$Me$_5$) C$_2$I]$_2$ | 60 | 12 | 46 | 53 | — | 0 |

[a]Conditions: 2 mmol acetophenone, 10 mmol ammonium formate, 0.04 mmol pre-catalyst, 4 ml 20% ammonia solution in MeOH;
[b]GC analysis of N-trifluoroacetyl derivative on a CP-Chirasil-Dex CB chiral column.

Examples 14

49.4 mg (0.08 mmol) of [Rh(C$_5$Me$_5$)Cl$_2$]$_2$ are initially added to 8 ml of methanol, 100 µl of triethylamine, and then 38.2 mg (0.18 mmol) of (1R,2R)-(+)-1,2-diphenyl-1,2-ethylendiamine are added and stirred for approx. 15 min. 1 ml (0.01 mmol) of catalyst solution were then added to a solution of 240 mg (2 mmol) of acetophenone in 5 ml of 20% ammonia solution in isopropanol and stirred for 12 hours at 60° C. in a pressure vessel. Under these conditions, 30% of the ketone was reacted to 1-phenylethylamine with an optical purity of 2% ee.

Example 15

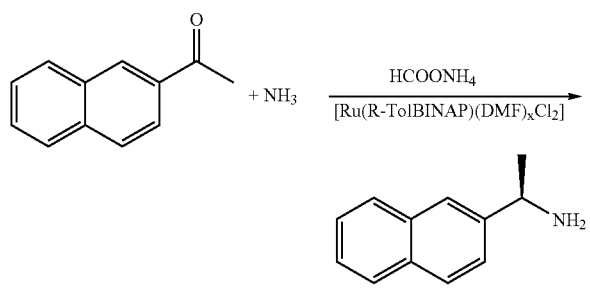

In a pressure vessel, 63 mg of ammonium formate, 5 mg (0.005 mmol) of [Ru(R-TolBINAP) (DMF)$_x$Cl$_2$] and 1 ml of 20% ammonia solution were added to 85 mg (0.5 mmol) of acetylnaphthalene and stirred for 24 hours at 90° C. After cooling, the mixture was investigated by gas chromatography. Under these conditions, 73% of the ketone was reacted to (R)-1-(naphthyl-2)ethylamine with an optical purity of 99% ee.

Examples 16–66

These examples are carried out in the same way as Example 15. Substrates, catalysts and the reaction results are given in Tables 3 and 4.

TABLE 3[a]

| | Substrate | Catalyst[b] | Educt | Amine | ee Amine % | Alcohol |
|---|---|---|---|---|---|---|
| 16 | 2-Acetylnaphthalene | A | 38 | 45 | 90 (S) | 6 |
| 17 | 2-Acetylnaphthalene | C | 38 | 61 | 99 (R) | 0 |
| 18 | 4-Hydroxyacetophenone | A | 0 | 31 | — | 0 |
| 19 | 4-Hydroxyacetophenone | B | 0 | 31 | — | 0 |
| 20 | 4-Hydroxyacetophenone | C | 0 | 28 | — | 0 |
| 21 | 4-Methylacetophenone | A | 0 | 66 | 10 (S) | 0 |
| 22 | 4-Methylacetophenone | B | 0 | 70 | 99 (R) | 0 |
| 23 | 4-Methylacetophenone | C | 0 | 76 | 99 (R) | 0 |
| 24 | 4-Methoxyacetophenone | A | 0 | 84 | 6 (S) | 6 |
| 25 | 4-Methoxyacetophenone | B | 0 | 88 | 99 (R) | 4 |
| 26 | 4-Methoxyacetophenone | C | 0 | 78 | 99 (R) | 16 |
| 27 | 4-Bromoacetophenone | A | 0 | 66 | 60 (S) | 2 |
| 28 | 4-Bromoacetophenone | B | 0 | 82 | 84 (R) | 0 |
| 29 | 4-Bromoacetophenone | C | 0 | 70 | 84 (R) | 0 |
| 30 | 1-Indanone | A | 0.7 | 2.0 | — | 0 |
| 31 | 1-Indanone | B | 0.5 | 4.6 | — | 0 |
| 32 | 1-Indanone | C | 1.9 | 5.7 | — | 0 |
| 33 | 2-Octanone | A | 9 | 20 | — | 22 |
| 34 | 2-Octanone | B | 6 | 28 | — | 8 |
| 35 | 2-Octanone | C | 5 | 24 | — | 22 |

[a]Conditions: 24 hours at 90° C., 0.5 mmol substrate, 1 mmol ammonium formate, 0.005 mmol catalyst, 1 ml 20% ammonia solution in MeOH;
[b]A = [(S-BINAP)RuCl$_2$(DMF)$_x$], B = [(R-TolBINAP)RuCl$_2$(DMF)$_x$], C = [(R-TolBINAP)RuCl$_2$(R-DAIPEN)].

TABLE 4[a]

| | Substrate | Catalyst[b] | Educt | Amine | Alcohol |
|---|---|---|---|---|---|
| 36 | 3-Methylacetophenone | A | 1 | 32 | 1 |
| 37 | 3-Methylacetophenone | B | 31 | 14 | 2 |

TABLE 4[a]-continued

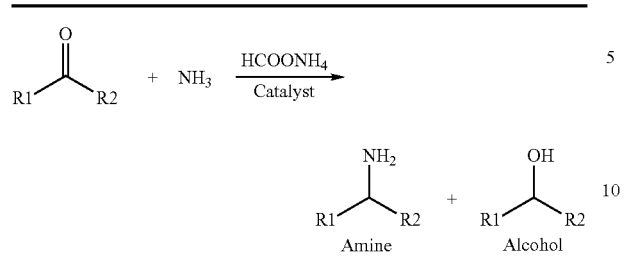

| | Substrate | Catalyst[b] | Educt | Amine | Alcohol |
|---|---|---|---|---|---|
| 38 | 3-Methylacetophenone | C | 1 | 76 | 1 |
| 39 | 4-Methylacetophenone | A | 0 | 28 | 0 |
| 40 | 4-Methylacetophenone | B | 50 | 23 | 0 |
| 41 | 4-Methylacetophenone | C | 0 | 61 | 0 |
| 42 | 4-Isopropylacetophenone | A | 0 | 35 | 0 |
| 43 | Propiophenone | A | 9 | 36 | 2 |
| 44 | Propiophenone | B | 13 | 2 | 0 |
| 45 | Propiophenone | C | 14 | 73 | 0 |
| 46 | 4-Acetylpyridine | A | 0 | 20 | 28 |
| 47 | 4-Acetylpyridine | B | 15 | 2 | 0 |
| 48 | 4-Acetylpyridine | C | 0 | 33 | 19 |
| 49 | 4-Methoxyacetophenone | A | 0 | 28 | 0 |
| 50 | 4-Methoxyacetophenone | B | 9 | 2 | 0 |
| 51 | 4-Methoxyacetophenone | C | 6 | 44 | 0 |
| 52 | 4-Chloroacetophenone | A | 0 | 51 | 0 |
| 53 | 4-Chloroacetophenone | C | 4 | 30 | 1 |
| 54 | 4-Bromoacetophenone | A | 0 | 37 | 3 |
| 55 | 4-Bromoacetophenone | B | 44 | 2 | 2 |
| 56 | 4-Bromoacetophenone | C | 7 | 31 | 0 |
| 57 | 1-Acetylnaphthalene | A | 16 | 7 | 5 |
| 58 | 1-Acetylnaphthalene | B | 65 | 6 | 1 |
| 59 | 1-Acetylnaphthalene | C | 30 | 4 | 3 |
| 60 | 2-Acetylnaphthalene | A | 0 | 20 | 0 |
| 61 | 2-Acetylnaphthalene | B | 37 | 10 | 2 |
| 62 | 2-Acetylnaphthalene | C | 3 | 54 | 0 |
| 63 | 2-Octanone | A | 0 | 21 | 3 |
| 64 | 2-Octanone | B | 0 | 17 | 10 |
| 65 | 2-Octanone | C | 0 | 37 | 3 |
| 66 | 2-Methylcyclohexanone | A | 0 | 42[c] | 0 |

[a]Conditions: 24 hours at 90° C., 0.5 mmol substrate, 1 mmol ammonium formate, 0.005 mmol catalyst, 1 ml 20% ammonia solution in MeOH;
[b]A = [(C$_5$Me$_5$)RuCl$_2$], B = [(COD)IrCl]$_2$, C = [(C$_5$Me$_5$)RhCl$_2$]$_2$;
[c]Sum of the two diastereomers.

Example 67

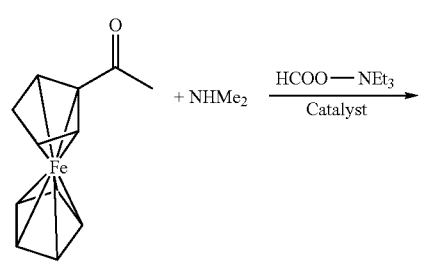

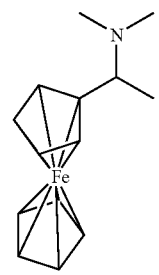

51.5 mg (0.16 mmol) of [Ru(COD) (methallyl)$_2$] and 122 mg (0.18 mmol) of R-TolBINAP were dissolved in 8 ml of CH$_2$Cl$_2$ and 48 μl of tetrafluoroboric acid in Et20 were added, and then 50 μl (1 mmol) of catalyst solution were added to a solution of 228 mg (1 mmol) of acetylferrocene and 433 mg of formic acid-triethylamine complex (5:2) in 1 ml of 5M dimethylamine solution in MeOH and vigorously stirred for 24 hours at 80° C. in a pressure vessel. Under these conditions, 36% of the ketone was reacted to the racemic (1-dimethylaminoethyl)-ferrocene.

Examples 68–74

These examples are carried out in the same way as Example 67. Catalysts and the reaction results are given in Table 5.

TABLE 5[a]

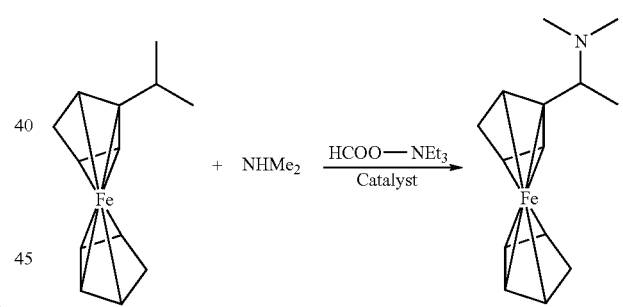

| | Catalyst | Ligand[c] | Educt | Product |
|---|---|---|---|---|
| 68 | [Ru(S-BINAP)Cl$_2$] | | 74 | 13 |
| 69 | [Ru(C$_4$H$_7$)$_2$(C$_8$H$_{12}$)] | S-Norphos | 75 | 12 |
| 70 | [Ru(Cymene)Cl$_2$]$_2$ | R-DPEA | 78 | 6 |
| 71 | [Ir(C$_8$H$_{14}$)$_2$Cl]$_2$ | S-Norphos | 75 | 21 |
| 72 | [Ir(C$_8$H$_{14}$)$_2$Cl]$_2$ | R-DPEA | 70 | 10 |
| 73 | [Ir(C$_5$Me$_5$)C$_2$I]$_2$ | R-DPEA | 72 | 17 |
| 74 | [Ir(DmaeInd)(C$_8$H$_{14}$)][b] | | 67 | 6 |

[a]Conditions: 24 hours at 90° C., 1 mmol acetylferrocene, 5 mmol formic acid-triethylamine, 0.001 mmol catalyst, 1 ml 5M dimethylamine solution in methanol;
[b]DmaeInd = dimethylaminoethyl)indenyl anion;
[c]S-Norphos = (2S,3S)-(+)-2,3-bis(diphenylphosphino)-bicyclo[2.2.1]hept-5-ene, R-DPEA= (1R,2R)-(+)-1,2-diphenyl-1,2-ethylendiamine;

Example 75

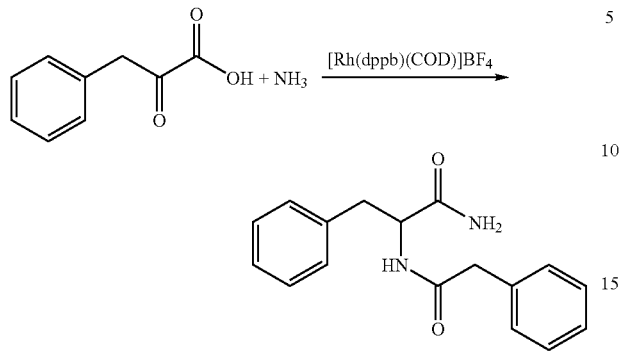

In a pressure vessel, 40 ml of methanol, which had been saturated with ammonia at 10° C., were added to 3.28 g 20 mmol) of phenylpyruvic acid and 72 mg (0.1 mmol) of [Rh(dppb)]BF$_4$ and stirred for 10 hours at 60° C. After evaporation of the solvent, the residue was taken up in 15 ml of hot methanol and the resulting solution was cooled, with N-phenylacetyl-phenylalanine amide crystallising out. Yield 1.42 g (50%).

Example 76

In a pressure vessel, 630 mg of ammonium formate, 3 mg (0.005 mmol) of [Rh(C$_5$Me$_5$)Cl$_2$]$_2$ and 10 ml of 20% ammonia solution were added to 106 mg (1 mmol) of benzaldehyde and stirred for 12 hours at 60° C. After cooling, the mixture was investigated by gas chromatography. With a conversion of 75%, a ratio of 60/15 benzylamine to dibenzylamine was found.

The invention claimed is:

1. A process for the production of amines by reductive hydride transfer amination, comprising reacting at least one ketone or at least one aldehyde with ammonia, at least one primary amine or at least one secondary amine in the presence of a hydrogen donor as reducing agent and a catalyst, wherein said catalyst is a transition metal complex, further wherein the metal in the transition metal complex catalyst is Rh or Ru.

2. A process according to claim 1, wherein the transition metal complex catalyst contains at least one ligand selected from the group consisting of mono- or bidentate nitrogen donor ligands, phosphorus donor ligands, cyclopentadienyl ligands, arene ligands, olefin ligands, alkyne ligands, heterocycloalkyl ligands, heteroaryl ligands, hydride ligands, alkyl ligands, carbonyl ligands and a mixture of these ligands.

3. A process according to claim 1, wherein the transition metal complex catalyst contains at least one mono- or bidentate ligand of formula (VI) or (VII),

wherein

L$^1$ and L$^2$, independently of one another, denote a coordinating group of formulae (VIII), (IX), (X) or (XII):

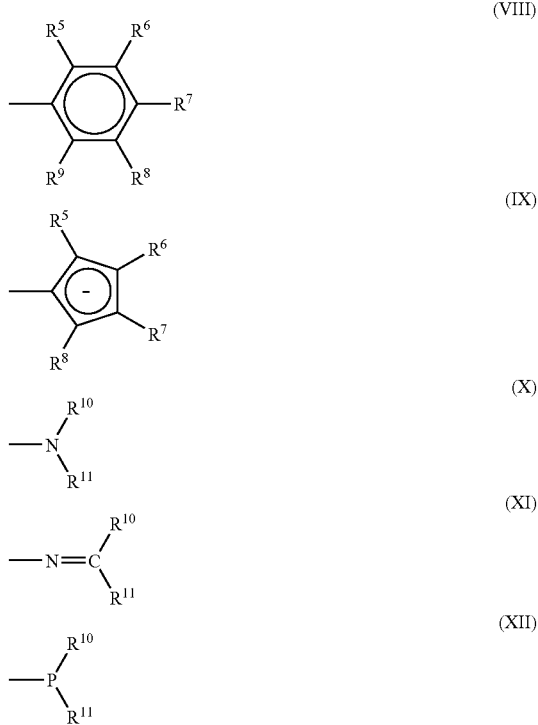

wherein

R$^5$ to R$^9$, independently of one another, are selected from the group consisting of hydrogen, (C$_1$–C$_{24}$)-alkyl, (C$_2$–C$_{24}$)-alkenyl, (C$_2$–C$_{24}$)-alkynyl, (C$_5$–C$_{10}$)-aryl CF$_3$, CO-alkyl-(C$_1$–C$_8$), CO-aryl-(C$_5$–C$_{10}$), CN, COOH, COOM, COO-alkyl-(C$_1$–C$_8$), COO-aryl-(C$_5$–C$_{10}$), C(=N-alkyl-(C$_1$–C$_8$))O-alkyl-(C$_1$–C$_8$), C(=N-aryl-(C$_5$–C$_{10}$))(O-alkyl-(C$_1$–C$_8$)), C(=N-alkyl-(C$_1$–C$_8$))(O-aryl-(C$_5$–C$_{10}$)), C(=N-aryl-(C$_5$–C$_{10}$))(O-aryl-(C$_5$–C$_{10}$)), CONH2, CONH-alkyl-(C$_1$–C$_8$), CON(alkyl-(C$_1$–C$_8$))$_2$, CONH-aryl-(C5–C$_{10}$), CON(aryl-(C$_5$–C$_{10}$))$_2$, PO(aryl-(C$_5$–C$_{10}$))$_2$, PO(alkyl-(C$_1$–C$_4$))$_2$, POH(alkyl-(C$_1$–C$_6$)), POH(aryl-(C$_5$–C$_{10}$)), PO(alkyl-(C$_1$–C$_4$))(O-alkyl-(C$_1$–C$_6$)), PO(alkyl-(C$_1$–C$_6$))(O-aryl-(C$_5$–C$_{10}$)), PO(aryl-(C$_5$–C$_{10}$))(O-alkyl-(C$_1$–C$_6$)), PO$_3$H$_2$, PO$_3$M$_2$, PO(O-alkyl-(C$_1$–C$_6$))$_2$, PO(O-aryl-(C$_5$–C$_{10}$))$_2$, PO(O-alkyl-(C$_1$–C$_6$))(O-aryl-(C$_5$–C$_{10}$)), SO$_3$H, SO$_3$M, SO$_3$-alkyl-(C$_1$–C$_4$), SO$_3$-aryl-(C$_5$–C$_{10}$), SO$_2$-alkyl-(C$_1$–C$_6$), SO$_2$-aryl-(C$_5$–C$_{10}$), SO-alkyl-(C$_1$–C$_8$), SO-aryl-(C$_5$–C$_{10}$), S-alkyl-(C$_1$–C$_8$), S-aryl-(C$_5$–C$_{10}$), SH, Si(alkyl-(C$_1$–C$_8$))$_3$, Si(C$_1$–C$_{10}$-alkyl/C$_5$–C$_{10}$-aryl)$_3$, NO$_2$, F, Cl, Br, I, O-alkyl-(C$_1$–C$_8$), O-aryl-(C$_5$–C$_{10}$), OH, NH$_2$, NH(alkyl-(C$_1$–C$_8$)), N(alkyl-(C$_1$–C$_8$))$_2$, NH(aryl-(C$_5$-Ci o)), NHCO-alkyl-(C$_1$–C$_4$), NHCO-aryl-(C$_5$–C$_{10}$), NHCOO-alkyl-(C$_1$–C$_4$), NHCOO-aryl-(C$_5$–C$_{10}$), OCO-alkyl-(C$_1$–C$_8$), OCO-aryl-(C$_5$–C$_{10}$), OPO(aryl-(C$_5$–C$_{10}$))$_2$, OPO(alkyl-(C$_1$–C$_4$))$_2$, OPOH(alkyl-(C$_1$–C$_6$)), OPO$_3$H$_2$, OPO$_3$M$_2$, OPO-alkyl-(C$_1$–C$_4$)(O-alkyl-(C$_1$–C$_6$)), OPO(O-alkyl-(C$_1$–C$_6$))$_2$, OPO(O-aryl-(C$_5$–C$_{10}$))$_2$, OSO$_3$H, OSO$_3$M, OSO$_2$—CF$_3$, OSO$_3$-alkyl-(C$_1$–C$_4$), OSO$_3$-aryl-(C$_5$–C$_{10}$), OSO$_2$-alkyl-(C$_1$–C$_6$), and OSO$_2$-aryl-(C$_5$–C$_{10}$), wherein M represents a cation selected from the group consisting of $Li^+$, $Na^+$, $K^+$, $Mg^{2+}$, $Ca^{2+}$, $NH_4^+$, $N(C_1-C_{10}$-alkyl$)_4^+$, and $N(C_1-C_{10}$-alkyl/$C_5-C_{10}$-aryl$)_4^+$, and wherein the residues $R_1$ to $R_2$, independently of one another, represent a hydrogen, $(C_1-C_{24})$-alkyl, $(C_2-C_{24})$-alkenyl, $(C_2-C_{24})$-alkynyl, $C_5-C_8$cycloalkenyl, $(C_5-C_{14})$-aryl, O-alkyl-$(C_1-C_8)$, O-aryl-$(C_5-C_{14})$, O-alkenyl-$(C_2-C_{24})$, O-alkynyl-$(C_2-C_{24})$, O-cycloalkenyl-$(C_5-C_8)$, O-aryl-$(C_5-C_{14})$, F, $NH_2$, NH(alkyl-$(C_1-C_8)$), NH-alkenyl-$(C_2-C_{24})$, NH-alkynyl-$(C_2-C_{24})$, NH-cycloalkenyl-$(C_5-C_8)$, NH-aryl-$(C_5-C_{14})$, N(alkyl-$(C_1-C_8))_2$, N(alkenyl-$(C_2-C_{24}))_2$, N(alkynyl-$(C_2-C_{24}))_2$, N(cycloalkenyl-$(C_5-C_8))_2$, N(alkyl-$(C_1-C_8)$)(aryl-$(C_5-C_{10})$), N(aryl-$(C_5-C_{10}))_2$, NHCO-alkyl-$(C_1-C_4)$, NHCO-alkenyl-$(C_2-C_{24})$, NHCO-alkynyl-$(C_2-C_{24})$, NHCO-cycloalkenyl-$(C_5-C_8)$, NHCO-aryl-$(C_5-C_{14})$, OCO-alkyl-$(C_1-C_4)$, OCO-alkenyl-$(C_2-C_{24})$, OCO-cycloalkenyl-$(C_5-C_8)$, OCO-aryl-$(C_5-C_{14})$, or $SO_2$-alkyl-$(C_1-C_6)$, $SO_2$-aryl-$(C_5-C_{10})$ residue and wherein all the above-mentioned substituents are optionally mono- or polysubstituted, and wherein two adjacent residues together optionally form saturated or unsaturated carbocyclic or heterocyclic groups having 3 to 15 atoms, with one to four nitrogen, phosphorus, silicon, sulfur or oxygen atoms, and wherein Q represents a bridge linking the unit $L^1$ with the unit $L^2$, of formula (XIII):

$$X^1-Z-X^2 \qquad (XIII)$$

wherein $X^1$ and $X^2$, independently of one another, represent a direct bond or a group $-O-$, $-S-$, or $-NR^{13}-$, wherein $R^{13}$ is one of the residues defined for $R^{10}-R^{12}$ and Z is a direct bond or a group of 1–16 carbon atoms linked by single or multiple bonds, wherein one to four carbon atoms are optionally replaced by heteroatoms, and wherein Z is optionally mono- or polysubstituted as stated for $R^5-R^9$ or optionally has a keto (=O), thioketo (=S) or imide substituent (=$NR^{14}$), wherein $R^{14}$ is one of the residues defined for $R^{10}-R^{12}$ and wherein two of the units $L^1$ with $R^{12}$ and $L^1$ or $L^2$ with Q are optionally linked together so that a saturated or unsaturated carbocyclic skeleton having 3 to 15 atoms or a saturated or unsaturated heterocyclic skeleton containing one to four nitrogen, phosphorus, silicon, sulfur or oxygen atoms is formed.

4. A process according to claim 3, wherein Q in formula (VII) represents an aliphatic, olefinic or acetylenic bridge consisting of one to fourteen carbon atoms, wherein one to four carbon atoms are optionally replaced with nitrogen or silicon atoms or one to two carbon atoms are optionally replaced with oxygen or sulfur atoms and wherein the individual binding links of the group, independently of one another, optionally carry substituents as defined for $R^3$ and $R^4$ or a keto (=O), thioketo (=S) or imide substituent (=$NR^{14}$) wherein $R^{14}$ is one of the residues defined for $R^{10}-R^{12}$ and wherein two of the units $L^1$, $L^2$ and Q are optionally linked together so that a saturated or unsaturated carbocyclic skeleton having 5 to 9 atoms or a saturated or unsaturated, heterocyclic skeleton containing one to four nitrogen, phosphorus, silicon, sulfur or oxygen atoms is formed.

5. A process according to claim 1, wherein the transition metal complex catalyst contains at least one mono-, bi-, tri- or tetradentate linear, branched or polycyclic, alkyne, olefin, conjugated or non-conjugated di- tri- or tetraene with two to twelve carbon atoms, wherein one to four carbon atoms are optionally replaced with nitrogen or silicon atoms or one to two carbon atoms are optionally replaced with oxygen or sulfur atoms and wherein the individual members of the group, independently of one another, optionally have substituents as defined for $R^5-R^9$ or a keto (=O), thioketo (=S) or imide substituent (=$NR^{14}$), wherein $R^{14}$ is one of the residues defined for $R^{10}-R^{12}$ wherein $R^5-R^9$, independently of one another, are selected from the group consisting of hydrogen, $(C_1-C_{24})$-alkyl, $(C_2-C_{24})$-alkenyl, $(C_2-C_{24})$-alkynyl, $(C_5-C_{10})$-aryl $CF_3$, CO-alkyl-$(C_1-C_8)$, CO-aryl-$(C_5-C_{10})$, CN, COOH, COOM, COO-alkyl-$(C_1-C_8)$, COO-aryl-$(C_5-C_{10})$, C(=N-alkyl-$(C_1-C_8)$)O-alkyl-$(C_1-C_8)$, C(=N-aryl-$(C_5-C_{10})$)(O-alkyl-$(C_1-C_8)$), C(=N-alkyl-$(C_1-C_8)$(O-aryl-$(C_5-C_{10})$), C(=N-aryl-$(C_5-C_{10})$)(O-aryl-$(C_5-C_{10})$), $CONH_2$, CONH-alkyl-$(C_1-C_8)$, CON(alkyl-$(C_1-C_8))_2$, CONH-aryl-$(C_5-C_{10})$, CON(aryl-$(C_5-C_{10}))_2$, PO(aryl-$(C_5-C_{10}))_2$, PO(alkyl-$(C_1-C_4))_2$, POH(alkyl-$(C_1-C_6)$), POH(aryl-$(C_5-C_{10})$), PO(alkyl-$(C_1-C_4)$)(O-alkyl-$(C_1-C_6)$), PO(alkyl-$(C_1-C_6)$)(O-aryl-$(C_5-C_{10})$), PO(aryl-$(C_5-C_{10})$)(O-alkyl-$(C_1-C_6)$), $PO_3H_2$, $PO_3M_2$, PO(O-alkyl-$(C_1-C_6))_2$, PO(O-aryl-$(C_5-C_{10}))_2$, PO(O-alkyl-$(C_1-C_6)$)(O-aryl-$(C_5-C_{10})$), $SO_3H$, $SO_3M$, $SO_3$-alkyl-$(C_1-C_4)$, $SO_3$-aryl-$(C_5-C_{10})$, $SO_2$-alkyl-$(C_1-C_6)$, $SO_3$-aryl-$(C_5-C_{10})$, SO-alkyl-$(C_1-C_8)$, SO-aryl-$(C_5-C_{10})$, $SO_2$-alkyl-$(C_1-C_8)$, S-aryl-$(C_5-C_{10})$, SH, Si(alkyl-$(C_1-C_8))_3$, Si$(C_1-C_{10}$-alkyl/$C_5-C_{10}$-aryl$)_3$, $NO_2$, F, Cl, Br, I, O-alkyl-$(C_1-C_8)$, O-aryl-$(C_5-C_{10})$, OH, $NH_2$, NH(alkyl-$(C_1-C_8)$), N(alkyl-$(C_1-C_8))_2$, NH(aryl-$(C_5-C_{10})$), NHCO-alkyl-$(C_1-C_4)$, NHCO-aryl-$(C_5-C_{10})$, NHCOO-alkyl-$(C_1-C_4)$, NHCOO-aryl-$(C_5-C_{10})$, OCO-alkyl-$(C_1-C_8)$, OCO-aryl-$(C_5-C_{10})$, OPO(aryl-$(C_5-C_{10}))_2$, OPO(alkyl-$(C_1-C_4))_2$, OPOH (alkyl-$(C_1-C_6)$), $OPO_3H_2$, $OPO_3M_2$, OPO-alkyl-$(C_1-C_4)$(O-alkyl-$(C_1-C_6)$), OPO(O-alkyl-$(C_1-C_6))_2$, OPO(O-aryl-$(C_5-C_{10}))_2$, $OSO_3H$, $OSO_3M$, $OSO_2$— $CF_3$, $OSO_3$-alkyl-$(C_1-C_4)$, $OSO_3$-aryl$(C_5-C_{10})$, $OSO_2$-alkyl-$(C_1-C_6)$, and $OSO_2$-aryl-$(C_5-C_{10})$, wherein M represents a cation selected from the group consisting of $Li^+$, $Na^+$, $K^+$, $Mg^{2+}$, $Ca^{2+}$, $NH_4^+$, $N(C_1-C_{10}$-alkyl$)_4^+$, and $N(C_1-C_{10}$-alkyl/$C_5-C_{10}$-aryl$)_4^+$, and wherein the residues $R^{10}-R^{12}$, independently of one another, represent a hydrogen, $(C_1-C_{24})$-alkyl, $(C_2-C_{24})$-alkenyl, $(C_2-C_{24})$-alkynyl, $C_5-C_8$cycloalkenyl, $(C_5-C_{14})$-aryl, O-alkyl-$(C_1-C_8)$, O-aryl-$(C_5-C_{14})$, O-alkenyl-$(C_2-C_{24})$, O-alkynyl-$(C_2-C_{24})$, O-cycloalkenyl-$(C_5-C_8)$, O-aryl-$(C_5-C_{14})$, F, NH(alkyl-$(C_1-C_8)$), NH-alkenyl-$(C_2-C_{24})$, NH-alkynyl-$(C_2-C_{24})$, NH-cycloalkenyl-$(C_5-C_8)$, NH-aryl-$(C_5-C_{14})$, N(alkyl-$(C_1-C_8))_2$, N(alkenyl-$(C_2-C_{24}))_2$, N(alkynyl-$(C_2-C_{24}))_2$, N(cycloalkenyl-$(C_5-C_8))_2$, N(alkyl-$(C_1-C_8)$)(aryl-$(C_5-C_{10})$), N(aryl-$(C_5-C_{10}))_2$, NHCO-alkyl-$(C_1-C_4)$, NHCO-alkenyl-$(C_2-C_{24})$, NHCO-alkynyl-$(C_2-C_{24})$, NHCO-cycloalkenyl-$(C_5-C_8)$, NHCO-aryl-$(C_5-C_{14})$, OCO-alkyl-$(C_1-C_4)$, OCO-alkenyl-$(C_2-C_{24})$, OCO-cycloalkenyl-$(C_5-C_8)$, OCO-aryl-$(C_5-C_{14})$, or $SO_2$-alkyl-$(C_1-C_6)$, $SO_2$-aryl$(C_5-C_{10})$ residue and wherein all the above-mentioned substituents are optionally mono- or polysubstituted, and wherein two adjacent residues together optionally form saturated or unsaturated carbocyclic or heterocyclic groups having 3 to 15 atoms, with one to four nitrogen, phosphorus, silicon, sulfur or oxygen atoms.

6. A process according to claim 1, wherein the transition metal complex catalyst has at least one mono- or bidentate polycyclic, saturated or unsaturated heterocyclic ligand having 3 to 15 atoms, with one to four oxygen, sulfur or nitrogen atoms, or a ($C_3$–$C_{13}$) heteroaromatic with one to four oxygen, sulfur, nitrogen or one to two phosphorus atoms, wherein the individual binding links, independently of one another, optionally carry substituents as defined for $R^5$–$R^9$ or a keto (=O), thioketo (=S) or imide substituent (=$NR_{14}$), wherein $R^{14}$ one of the residues defined for $R^{10}$–$R^{12}$, wherein $R^5$–$R^9$, independently of one another, are selected from the group consisting of hydrogen, ($C_1$–$C_{24}$)-alkyl, ($C_2$–$C_{24}$)-alkenyl, ($C_2$–$C_{24}$)-alkynyl, ($C_5$–$C_{10}$)-aryl, $CF_3$, CO-alkyl-($C_1$–$C_8$), CO-aryl-($C_5$–$C_{10}$), CN, COOH, COOM, COO-alkyl-($C_1$–$C_8$), COO-aryl-($C_5$–$C_{10}$), C(=N-alkyl-($C_1$–$C_8$))O-alkyl-($C_1$–$C_8$)), C(=N-aryl-($C_5$–$C_{10}$))(O-alkyl-($C_1$–$C_8$)), C(=N-alkyl-($C_1$–$C_8$))O-aryl-($C_5$–$C_{10}$)), C(=N-aryl-($C_5$–$C_{10}$))(O-aryl-($C_5$–$C_{10}$)), $CONH_2$, CONH-alkyl-($C_{C1}$–$C_8$), CON(alkyl-($C_1$–$C_8$))$_2$, CONH-aryl-($C_5$–$C_{10}$), CON(aryl-($C_5$–$C_{10}$))$_2$, PO(aryl-($C_5$–$C_{10}$))$_2$, PO(alkyl-($C_1$–$C_4$))$_2$, POH(alkyl-($C_1$–$C_6$)), POH(aryl-($C_5$–$C_{10}$)), PO(alkyl-($C_1$–$C_4$))(O-alkyl-($C_1$–$C_6$)), PO(alkyl-($C_1$–$C_6$))(O-aryl-($C_5$–$C_{10}$)), PO(alkyl-($C_1$–$C_4$))(O-alkyl-($C_1$–$C_6$)), $PO_3H_2$, $PO_3M_2$, PO(O-alkyl-($C_1$–$C_6$))$_2$, PO(O-aryl-($C_5$–$C_{10}$))$_2$, PO(O-alkyl-($C_1$–$C_6$))(O-aryl-($C_5$–$C_{10}$)), $SO_3H$, $SO_3M$, $SO_3$-alkyl-($C_1$–$C_4$), $SO_3$-aryl-($C_5$–$C_{10}$), $SO_2$-alkyl-($C_1$–$C_6$), $SO_2$-aryl-($C_5$–$C_{10}$), SO-alkyl-($C_1$–$C_8$), SO-aryl-($C_5$–$C_{10}$), S-alkyl-($C_1$–$C_8$), S-aryl-($C_5$–$C_{10}$), SH, Si(alkyl-($C_1$–$C_8$))$_3$, Si($C_1$–$C_{10}$-alkyl/$C_5$–$C_{10}$-aryl)$_3$, $NO_2$, F, Cl, Br, I, O-alkyl-($C_1$–$C_8$), O-aryl-($C_5$–$C_{10}$), OH, $NH_2$, NH(alkyl-($C_1$–$C_8$)), N(alkyl-($C_1$–$C_8$))$_2$, NH(aryl-($C_5$–$C_{10}$)), NHCO-alkyl-($C_1$–$C_4$), NHCO-aryl-($C_5$–$C_{10}$), NHCOO-alkyl-($C_1$–$C_4$), NHCOO-aryl-($C_5$–$C_{10}$), OCO-alkyl-($C_1$–$C_8$), OCO-aryl-($C_5$–$C_{10}$), OPO(aryl-($C_5$–$C_{10}$))$_2$, OPO(alkyl-($C_1$–$C_4$)$_2$, OPOH(alkyl-($C_1$–$C_6$)), $OPO_3H_2$, $OPO_3M_2$, OPO-alkyl-($C_1$–$C_4$)(O-alkyl-($C_1$–$C_6$)), OPO(O-alkyl-($C_1$–$C_6$))$_2$, OPO(O-aryl-($C_5$–$C_{10}$))$_2$, $OSO_3H$, $OSO_3M_2$, $OSO_2$—$CF_3$, $OSO_3$-alkyl-($C_1$–$C_4$), $OSO_3$-aryl-($C_5$–$C_{10}$), $OSO_2$-alkyl-($C_1$–$C_6$), and $OSO_2$-aryl-($C_5$–$C_{10}$), wherein M represents a cation selected from the group consisting of $Li^+$, $Na^+$, $K^+$, $Mg^{2+}$, $Ca^{2+}$, $NH_4^+$, $N(C_1$–$C_{10}$-alkyl)$_4^+$, and $N(C_1$–$C_{10}$-alkyl/$C_5$–$C_{10}$-aryl)$_4^+$, and wherein the residues $R^{10}$–$R^{12}$, independently of one another, represent a hydrogen. ($C_1$–$C_{24}$)-alkyl, ($C_2$–$C_{24}$)-alkenyl, ($C_2$–$C_{24}$)-alkynyl, -$C_5$–$C_8$cycloalkenyl, ($C_5$–$C_{14}$)aryl, O-alkyl-($C_1$–$C_8$), O-aryl-($C_5$–$C_{14}$), O-alkenyl-($C_2$–$C_{24}$), O-alkynyl-($C_2$–$C_{24}$), O-cycloalkenyl-($C_5$–$C_8$), O-aryl-($C_5$–$C_{14}$), F, $NH_2$, NH(alkyl-($C_1$–$C_8$)), NH-alkenyl-($C_2$–$C_{24}$), NH-alkynyl-($C_2$–$C_{24}$), NH-cycloalkenyl-($C_5$–$C_8$), NH-aryl-($C_5$–$C_{14}$), N(alkyl-($C_1$–$C_8$))$_2$, N(alkenyl-($C_2$–$C_{24}$))$_2$, N(alkynyl-($C_2$–$C_{24}$))$_2$, N(cycloalkenyl-($C_5$–$C_8$)$_2$, N(alkyl-($C_1$–$C_8$))(aryl-($C_5$–$C_{10}$)), N(aryl-($C_5$–$C_{10}$))$_2$, NHCO-alkyl-($C_1$–$C_4$), NHCO-alkenyl-($C_2$–$C_{24}$), NHCO-alkynyl-($C_2$–$C_{24}$), NHCO-cycloalkenyl-($C_5$–$C_8$), NHCO-aryl-($C_5$–$C_{14}$), OCO-alkyl-($C_1$–$C_4$), OCO-alkenyl-($C_2$–$C_{24}$), OCO-cycloalkenyl-($C_5$–$C_8$), OCO-aryl-($C_5$–$C_{14}$), or $SO_2$-alkyl-($C_1$–$C_{10}$), $SO_2$-aryl($C_5$–$C_8$) residue and wherein all the above-mentioned substituents are optionally mono- or polysubstituted, and wherein two adjacent residues together optionally form saturated or unsaturated carbocyclic or heterocyclic groups having 3 to 15 atoms, with one to four nitrogen, phosphorus, silicon, sulfur or oxygen atoms.

7. A process according to claim 1, wherein the transition metal complex catalyst contains a ligand selected from the group consisting of DAIPEN, BINAP, Dnaelnd, dppb, dcypb, (R,R)-DIPAMP; (R)-Norphos; (R,R)-CHIRAPHOS; (R,R)-DEGUPHOS; (R)-CyGanterPhos; (R,R)-Me-DUPHOS; (R,R)-Et-DUPHOS; (R,R)-Me-BPE; (R,R)-Et-BPE; (R)-bis(MePheP)benzene; (R)-PROPHOS; (R,R)-SKEWPHOS; (S)-Phos4; (R,S)-Cy-Fc-etdpp; (R,S)-Cy-Fc-etdCyP; (R,S)-Ph-Fc-etdtBuP; (R,S)-JOSIPHOS; (R)-carboxybutyl-BIPHEP; (R)-BINAP; (R)-Tol-BINAP; ((R)-2,2'-bis(di-p-tolylphosphino)-1,1'-binaphthyl); (R)-MeO-BIPHEP; (R)-p-Tol-MeO-BIPHEP; (S,S)-1,2-(BDPPmethyl)-cyclohexane; (S,S)-DIOP; (S)-MOD-DIOP; (R)-MeAAPHOS; (S,S)-BPPM-H; (S,S)-BPPM; (R,R)-phenyl-CAPP; (R)-NAPHOS; Ph-β-Glup; Ph-β-Glup-OH; (phenyl 2,3-bis(O-diphenylphosphino)-β-D-glucopyranoside); DPOE; (R,R)-bdpch; (R,R)-CYLOPP-2-Me; (R,R)-CYCLOPP-4-CF3; (R,R)-CYCLOPP-3,5-Cl; (R,R)-CYCLOPP-3,5-CF3; (R,R)-CYCLOPP-3,5-F; CARBOPHOS-3,5-Me2Ph; GLUCOPHOS-Ph-3,5-Me; R-POP-Bz; (R,S)-Phos3; (5)-CyCy-OxoPRONOP; (S)-Cy,Cy-PRONOP; (S)-CyCyisoALANOP; (R)-PROPRAPHOS; PROPRAHOS analogue (R)-Cyp-PPP; (R)-PN-Ph; (S)-PN-iPr; (S)-PN-iPr-Me; (S)-PN-tBu; (R)-QUINAP; and (R,R)-(S,S)-EtTRAP.

8. A process according to claim 1, wherein the transition metal complex catalyst is produced from at least one transition metal salt or a transition metal pre-complex containing at least one metal from the eighth subgroup and at least one ligand of the formulae (VI) or (VII):

$L^1$—$R^{12}$ (VI)

$L^1$—Q—$L^2$ (VII)

wherein $L^1$ and $L^2$, independently of one another, denote a coordinating group of formulae (VIII), (IX), (X), (XI) or (XII):

(VIII)

(IX)

(X)

(XI)

-continued

(XII)

wherein $R^5$–$R^9$ to independently of one another, are selected from the group consisting of hydrogen, $(C_1$–$C_{24})$-alkyl, $(C_2$–$C_{24})$-alkenyl, $(C_2$–$C_{24})$-alkynyl, $(C_5$–$C_{10})$-aryl, $CF_3$, CO-alkyl-$(C_1$–$C_8)$, CO-aryl-$(C_5$–$C_{10})$, CN, COOH, COOM, COO-alkyl-$(C_1$–$C_8)$, COO-aryl-$(C_5$–$C_{10})$, C(=N-alkyl-$(C_1$–$C_8))$O-alkyl-$(C_1$–$C_8)$, C(=N-aryl-$(C_5$–$C_{10}))(O$-alkyl-$(C_1$–$C_8))$, C(=N-alkyl-$(C_1$–$C_8))(O$-aryl-$(C_5$–$C_{10}))$, C(=N-aryl-$(C_5$–$C_{10}))(O$-aryl-$(C_5$–$C_{10}))$, $CONH_2$, CONH-alkyl-$(C_1$–$C_8)$, CON(alkyl-$(C_1$–$C_8))_2$, CONH-aryl-$(C_5$–$C_{10})$, CON(aryl-$(C_5$–$C_{10}))_2$, PO(aryl-$(C_5$–$C_{10}))_2$, PO(alkyl-$(C_1$–$C_4))_2$, POH(alkyl-$(C_1$–$C_6))$, POH(aryl-$(C_5$–$C_{10}))$, PO(alkyl-$(C_1$–$C_4))(O$-alkyl-$(C_1$–$C_6))$, PO(alkyl-$(C_1$–$C_6))(O$-aryl-$(C_5$–$C_{10}))$, PO(aryl-$(C_5$–$C_{10}))(O$-alkyl-$(C_1$–$C_6))$, $PO_3H_2$, $PO_3M_2$, PO(O-alkyl-$(C_1$–$C_6))_2$, PO(O-aryl-$(C_5$–$C_{10}))_2$, PO(O-alkyl-$(C_1$–$C_6))(O$-aryl-$(C_5$–$C_{10}))$, $SO_3H$, $SO_3M$, $SO_3$-alkyl-$(C_1$–$C_4)$, $SO_3$-aryl-$(C_5$–$C_{10})$, $SO_2$-alkyl-$(C_1$–$C_6)$, $SO_2$-aryl-$(C_5$–$C_{10})$, SO-alkyl-$(C_1$–$C_8)$, SO-aryl-$(C_5$–$C_{10})$, S-alkyl-$(C_1$–$C_8)$, S-aryl-$(C_5$–$C_{10})$, SH, Si(alkyl-$(C_1$–$C_8))_3$, Si$(C_1$–$C_{10}$-alkyl/$C_5$–$C_{10}$-aryl$)_3$, $NO_2$, F, Cl, Br, I, O-alkyl-$(C_1$–$C_8)$, O-aryl-$(C_5$–$C_{10})$, OH, $NH_2$, NH(alkyl-$(C_1$–$C_8))$, N(alkyl-$(C_1$–$C_8))_2$, NH(aryl-$(C_5$–$C_{10}))$, NHCO-alkyl-$(C_1$–$C_4)$, NHCO-aryl-$(C_5$–$C_{10})$, NHCOO-alkyl-$(C_1$–$C_4)$, NHCOO-aryl-$(C_5$–$C_{10})$, OCO-alkyl-$(C_1$–$C_8)$, OCO-aryl-$(C_5$–$C_{10})$, OPO(aryl-$(C_5$–$C_{10}))_2$, OPO(alkyl-$(C_1$–$C_4))_2$, OPOH(alkyl-$(C_1$–$C_6))$, $OPO_3H_2$, $OP)_3M_2$, OPO-alkyl-$(C_1$–$C_4)(O$-alkyl-$(C_1$–$C_6))$, OPO(O-alkyl-$(C_1$–$C_6))_2$, OPO(O-aryl-$(C_5$–$C_{10}))_2$, $OSO_3H$, $OSO_3M$, $OSO_2$-$CF_3$, $OS_3$-alkyl-$(C_1$–$C_4)$, $OSO_3$-aryl-$(C_5$–$C_{10})$, $OSO_2$-alkyl-$(C_1$–$C_6)$, and $OSO_2$-aryl-$(C_5$–$C_{10})$, wherein M represents a cation selected from group consisting of $Li^+$, $Na^+$, $K^+$, $Mg^{2+}$, $Ca^{2+}$, $NH_4^+$, $N(C_1$–$C_{10}$-alkyl$)_4^+$, and $N(C_1$–$C_{10}$-alkyl/$C_5$–$C_{10}$-aryl$)_4^+$, and wherein the residues $R^{10}$ to $R^{12}$, independently of one another, represent a hydrogen, $(C_1$–$C_{24})$-alkyl, $(C_2$–$C_{24})$-alkenyl, $(C_2$–$C_{24})$-alkynyl, $C_5$–$C_8$cycloalkenyl, $(C_5$–$C_{14})$-aryl, O-alkyl-$(C_1$–$C_8)$, O-aryl-$(C_5$–$C_{14})$, O-alkenyl-$(C_2$–$C_{24})$, O-alkynyl-$(C_2$–$C_{24})$, O-cycloalkenyl-$(C_5$–$C_8)$, O-aryl-$(C_5$–$C_{14})$, F, $NH_2$, NH(alkyl-$(C_1$–$C_8))$, NH-alkenyl-$(C_2$–$C_{24})$, NH-alkynyl-$(C_2$–$C_{24})$, NH-cycloalkenyl-$(C_5$–$C_8)$, NH-aryl-$(C_5$–$C_{14})$, N(alkyl-$(C_1$–$C_8))_2$, N(alkenyl-$(C_2$–$C_{24}))_2$, N(alkynyl-$(C_2$–$C_{24}))_2$, N(cycloalkenyl-$(C_5$–$C_8))_2$, N(alkyl-$(C_1$–$C_8))(aryl$-$(C_5$–$C_{10}))$, N(aryl-$(C_5$–$C_{10}))_2$, NHCO-alkyl-$(C_1$–$C_4)$, NHCO-alkenyl-$(C_2$–$C_{24})$, NHCO-alkynyl-$(C_2$–$C_{24})$, NHCO-cycloalkenyl-$(C_5$–$C_8)$, NHCO-aryl-$(C_5$–$C_{14})$, OCO-alkyl-$(C_1$–$C_4)$, OCO-alkenyl-$(C_2$–$C_{24})$, OCO-cycloalkenyl-$(C_5$–$C_8)$, OCO-aryl-$(C_5$–$C_{14})$, or $SO_2$-alkyl-$(C_1$–$C_6)$, $SO_2$-aryl-$(C_5$–$C_{10})$ residue and wherein all the above-mentioned substituents are optionally mono- or polysubstituted, and wherein two adjacent residues together optionally form saturated or unsaturated carbocyclic or heterocyclic groups having 3 to 15 atoms, with one to four nitrogen, phosphorus, silicon, sulfur or oxygen atoms, and wherein Q represents a bridge linking the unit $L^1$ with the unit $L^2$, of the formula (XIII):

wherein $X^1$ and $X^2$, independently of one another, represent a direct bond or a group —O—, —S—, or —$NR^{13}$—, wherein $R^{13}$ is one of the residues defined for $R^{10}$–$R^{12}$ and Z is a direct bond or a group of 1–16 carbon atoms linked by single or multiple bonds, wherein one to four carbon atoms is optionally replaced by heteroatoms, and wherein Z is optionally mono- or polysubstituted as stated for $R^5$–$R^9$ or optionally has a keto (=O), thioketo (=S) or imide substituent (=$NR^{14}$), wherein $R^{14}$ is one of the residues defined for $R^{10}$–$R^{12}$ and wherein two of the units $L^1$ with $R^{12}$ and $L^1$ or $L^2$ with Q is optionally linked together so that a saturated or unsaturated carbocyclic skeleton having 3 to 15 atoms or a saturated or unsaturated heterocyclic skeleton containing one to four nitrogen, phosphorus, silicon, sulfur or oxygen atoms is formed.

9. A process according to claim 1, wherein the hydrogen donor is selected from the group consisting of primary and secondary alcohols, hydroaromatic and heterocyclic compounds, terpenes, N-benzylaniline, hydrazine, trialkylsilanes, trialkyltin hydrides, carboxylic acids and phosphinous acids and their esters, amides and ammonium salts and mixtures thereof.

10. A process according to claim 1, wherein the hydrogen donor is a carboxylic acid or a primary or secondary alcohol containing 1 to 20 carbon atoms.

11. A process according to claim 1, wherein the hydrogen donor is selected from the group consisting of isopropanol, ammonium formate, triethylammonium formate and formic acid-triethylamine mixture.

12. A process according to claim 1, comprising reacting at least one carbonyl compound of formula (I)

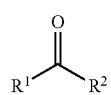
(I)

wherein $R^1$ and $R^2$, independently of one another, are each selected from the group consisting of hydrogen, $(C_1$–$C_{24})$-alkyl, $(C_2$–$C_{24})$-alkenyl, $(C_2$–$C_{24})$-alkynyl, $(C_5$–$C_{10})$-aryl, $CF_3$, CHO, CO-alkyl-$(C_1$–$C_8)$, CO-aryl-$(C_5$–$C_{10})$, COO-alkyl-$(C_1$–$C_8)$, COO-aryl-$(C_5$–$C_{10})$, C(=N-alkyl-$(C_1$–$C_8))$O-alkyl-$(C_1$–$C_8)$, C(=N-aryl-$(C_6$–$C_{10}))$O-alkyl-$(C_1$–$C_8)$, C(=N-alkyl-$(C_1$–$C_8))$O-aryl-$(C_5$–$C_{10})$, C(=N-aryl-$(C_5$–$C_{10}))$O-aryl-$(C_5$–$C_{10})$, $CONH_2$, CONH-alkyl-$(C_1$–$C_8)$, CON(alkyl-$(C_1$–$C_8))_2$, CONH-aryl-$(C_5$–$C_{10})$, CON(aryl-$(C_5$–$C_{10}))_2$, PO(aryl-$(C_5$–$C_{10}))_2$, PO(alkyl-$(C_1$–$C_4))_2$, PO(alkyl-$(C_1$–$C_4))(O$-alkyl-$(C_1$–$C_6))$, PO(alkyl-$(C_1$–$C_6))(O$-aryl-$(C_5$–$C_{10}))$, PO(aryl-$(C_5$–$C_{10}))(O$-alkyl-$(C_1$–$C_6))$, PO(O-alkyl-$(C_1$–$C_6))_2$, PO(O-aryl-$(C_5$–$C_{10}))_2$, PO(O-alkyl-$(C_1$–$C_6))(O$-aryl-$(C_5$–$C_{10}))$, $SO_2$-O-alkyl-$(C_1$–$C_4)$, $SO_2$-O-aryl-$(C_5$–$C_{10})$, $SO_2$-alkyl-$(C_1$–$C_6)$, $SO_2$-aryl-$(C_5$–$C_{10})$, SO-alkyl-$(C_1$–$C_8)$, SO-aryl-$(C_5$–$C_{10})$ or Si(alkyl-$(C_1$–$C_8))_3$, and Si$(C_1$–$C_{10}$-alkyl/$C_5$–$C_{10}$-aryl$)_3$, CH(O-alkene- ($C_2$–$C_8$)—O), C(O-alkene-($C_2$–$C_8$)—O)-alkyl-($C_1$–$C_8$), C(O-alkene-($C_2$–$C_8$)—O)-aryl-($C_5$–$C_{10}$), CH(O-alkyl-($C_1$–$C_8$))$_2$, C(O-alkyl-($C_1$–$C_8$))$_2$-alkyl-($C_1$–$C_8$), C(O-alkyl-($C_1$–$C_8$))$_2$-aryl-($C_5$–$C_{10}$), CHO, CN, COOH, COOM, POH(alkyl-($C_1$–$C_6$)), POH(aryl-($C_5$–$C_{10}$)), PO$_3$H$_2$, PO$_3$M$_2$, SO$_3$H, and SO$_3$M, wherein M represents a cation selected from the group consisting of Li$^+$, Na$^+$, K$^+$, Mg$^{2+}$, Ca$^{2+}$, NH$_4^+$, N($C_1$–$C_{10}$-alkyl)$_4^+$, and N(H/$C_1$–$C_{10}$-alkyl/$C_6$–$C_{10}$-aryl)$_4^+$; wherein alkyl wherein alkyl denotes a linear or branched, aliphatic or cyclic residue, alkenyl denotes an olefinic hydrocarbon, alkynyl denotes an acetylene hydrocarbon and aryl denotes an aromatic residue, wherein up to 4 carbon atoms in each case are optionally replaced by a nitrogen, phosphorus, silicon, sulfur or oxygen atom, further wherein R$^1$ and R$^2$ are optionally linked by covalent bonds, so that R$^1$ and R$^2$ optionally each form a saturated or unsaturated carbocyclic or heterocyclic unit having 3 to 15 atoms, with one to four nitrogen, phosphorus, silicon, sulfur or oxygen atoms.

with ammonia, at least one primary amine or at least one secondary amine of formula (II)

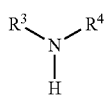

(II)

R$^3$ to R$^4$, independently of one another, is selected from the group consisting of hydrogen, ($C_1$–$C_{24}$)-alkyl, ($C_2$–$C_{24}$)-alkenyl, ($C_2$–$C_{24}$)-alkynyl, ($C_5$–$C_{10}$)-aryl, CF$_3$, CHO, CO-alkyl-($C_1$–$C_8$), CO-aryl-($C_5$–$C_{10}$), COO-alkyl-($C_1$–$C_8$), COO-aryl-($C_5$–$C_{10}$), C(=N-alkyl-($C_1$–$C_8$))O-alkyl-($C_1$–$C_8$), C(=N-aryl-($C_6$–$C_{10}$))O-alkyl-($C_1$–$C_8$), C(=N-alkyl-($C_1$–$C_8$))O-aryl-($C_5$–$C_{10}$), C(=N-aryl-($C_5$–$C_{10}$))O-aryl-($C_5$–$C_{10}$), CONH$_2$, CONH-alkyl-($C_1$–$C_8$), CON(alkyl-($C_1$–$C_8$))$_2$, CONH-aryl-($C_5$–$C_{10}$), CON(aryl-($C_5$–$C_{10}$))$_2$, PO(aryl-($C_5$–$C_{10}$))$_2$, PO(alkyl-($C_1$–$C_4$))$_2$, PO(alkyl-($C_1$–$C_4$))(O-alkyl-($C_1$–$C_6$)), PO(alkyl-($C_1$–$C_6$))(O-aryl-($C_5$–$C_{10}$))$_2$, PO(aryl-($C_5$–$C_{10}$))(O-alkyl-($C_1$–$C_1$–$C_6$)), PO(O-alkyl-($C_1$–$C_6$))$_2$, PO(O-aryl-($C_5$–$C_{10}$))$_2$, PO(alkyl-($C_1$–$C_6$))(O-aryl-($C_5$–$C_{10}$)), SO$_2$—O-alkyl-($C_1$–$C_4$), SO$_2$—O-aryl-($C_5$–$C_{10}$), SO$_2$-alkyl-($C_1$–$C_6$), SO$_2$-aryl-($C_5$–$C_{10}$), SO-alkyl-($C_1$–$C_8$), SO-aryl-($C_5$–$C_{10}$) or Si(alkyl-($C_1$–$C_8$))$_3$, and Si($C_1$–$C_{10}$-alkyl/$C_5$–$C_{10}$-aryl)$_3$, O-alkyl-($C_1$–$C_8$), O-aryl-($C_5$–$C_{10}$), fluorine, OH, NH$_2$, NH(alkyl-($C_1$–$C_8$)), N(alkyl-($C_1$–$C_8$))$_2$, NH(aryl-($C_5$–$C_{10}$)), NHCO-alkyl-($C_1$–$C_4$), NHCO-aryl-($C_5$–$C_{10}$), NHCOO-alkyl-($C_1$–$C_8$), and NHCOO-aryl-($C_5$–$C_{10}$), wherein alkyl denotes a linear or branched, aliphatic or cyclic residue, alkenyl denotes an olefinic hydrocarbon, alkynyl denotes an acetylene hydrocarbon and aryl denotes an aromatic residue, wherein up to 4 carbon atoms in each case can be are optionally replaced by a nitrogen, phosphorus, silicon, sulfur or oxygen atom, further wherein R$^1$ and R$^2$ as well as R$^3$ and R$^4$ are optionally linked by covalent bonds, so that R$^3$ and R$^4$ optionally each form a saturated or unsaturated carbocyclic or heterocyclic unit having 3 to 15 atoms, with one to four nitrogen, phosphorus, silicon, sulfur or oxygen atoms;

to form at least one compound of general formula (III),

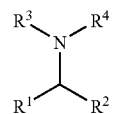

(III)

wherein R$^1$, R$^2$, R$^3$ and R$^4$ have the meanings set forth above.

13. A process according to claim 12, wherein the alkyl, alkenyl, alkynyl, aryl, heterocycloalkyl and heteroaryl groups, comprise at least substituent selected from the group consisting of hydrogen, ($C_1$–$C_{20}$)-alkyl, ($C_2$–$C_{20}$)-alkenyl, ($C_1$–$C_{10}$)-haloalkyl, ($C_3$–$C_8$)-cycloalkyl, ($C_5$–$C_8$)-cycloalkenyl, ($C_2$–$C_9$)-heterocycloalkyl, ($C_1$–$C_9$)-heterocycloalkenyl, ($C_5$–$C_{14}$)-aryl, ($C_2$–$C_{13}$)-heteroaryl, wherein the number of heteroatoms selected from the group N, O, S, is optionally one to four, fluorine, chlorine, bromine, iodine, OH, NO$_2$, CF$_3$, O-alkyl-($C_1$–$C_8$), O-aryl-($C_5$–$C_{10}$), OCO-alkyl-($C_1$–$C_8$), OCO-aryl-($C_5$–$C_{10}$), NH$_2$, NH(alkyl-($C_1$–$C_8$)), NH(aryl-($C_5$–$C_{10}$)), N(alkyl-($C_1$–$C_8$))$_2$, N(aryl-($C_5$–$C_{10}$))$_2$, NHCO-alkyl-($C_1$–$C_8$NHCO-aryl-($C_5$–$C_{10}$), CH(O-alkene-($C_2$–$C_6$)—O), C(O-alkene-($C_2$–$C_6$)—O)-alkyl-($C_1$–$C_8$), C(O-alkene-($C_2$–$C_6$)—O)-aryl-($C_5$–$C_{10}$), CH(O-alkyl-($C_1$–$C_8$))$_2$, C(O-alkyl-($C_1$–$C_8$))$_2$-alkyl-($C_1$–$C_8$), C(O-alkyl-($C_1$–$C_8$))$_2$-aryl-($C_5$–$C_{10}$), CHO, CO-alkyl-($C_1$–$C_8$), CO-aryl-($C_5$–$C_{10}$), CN, COOH, COOM, COO-alkyl-($C_1$–$C_8$), C(=N-alkyl-($C_1$–$C_8$))O-alkyl-($C_1$–$C_8$), C(=N-aryl-($C_5$–$C_{10}$))O-alkyl-($C_1$–$C_8$), C(=N-alkyl-($C_1$–$C_8$))O-aryl-($C_5$–$C_{10}$), C(=N-aryl-($C_5$–$C_5$–$C_{10}$), CONH$_2$, CO-alkyl-($C_1$–$C_8$), NHCOH, NHCOO-alkyl-($C_1$–$C_4$), CO-aryl-($C_5$–$C_{10}$), COO-aryl-($C_5$–$C_{10}$), CHCH—COO-alkyl-($C_1$–$C_8$), CN, COOH, COOM, CHCHCO$_2$H, P(aryl-($C_5$–$C_{10}$))$_2$, P(alkyl-($C_1$–$C_8$))$_2$, PO(aryl-($C_5$–$C_{10}$))$_2$, PO(alkyl-($C_1$–$C_4$))(O-alkyl-($C_1$–$C_6$)), PO(O-alkyl-($C_1$–$C_6$))$_2$, OPO(aryl)$_2$-($C_5$–$C_{10}$), OPO(alkyl)$_2$-($C_1$–$C_4$), OPOH(alkyl-($C_1$–$C_6$)), OPO$_3$H$_2$, OPO$_3$M$_2$, OPO(alkyl-($C_1$–$C_4$))(O-alkyl-($C_1$–$C_6$)), OPO(aryl-($C_5$–$C_{10}$))(O-alkyl-($C_1$–$C_6$)), OPO(O-alkyl-($C_1$–$C_6$))$_2$, OPO(O-aryl-($C_5$–$C_{10}$))$_2$, SO$_3$H, SO$_3$M, SO$_2$—O-alkyl-($C_1$–$C_4$), SO$_2$—O-aryl-($C_5$–$C_{10}$), SO$_2$-alkyl-($C_1$–$C_6$), SO$_2$-aryl-($C_5$–$C_{10}$), SO-alkyl-($C_1$–$C_6$)), SO-aryl-($C_5$–$C_{10}$), OSO$_3$H, OSO$_3$M, OSO$_2$—O-alkyl-($C_1$–$C_4$), OSO$_2$-alkyl-($C_1$–$C_6$) or Si(alkyl-($C_1$–$C_8$))$_3$, and Si($C_1$–$C_8$-alkyl/$C_5$–$C_{10}$-aryl)$_3$, wherein M represents a cation selected from the group consisting of Li$^+$, Na$^+$, K$^+$, Mg$^{2+}$, Ca$^{2+}$, NH$_4^+$, N($C_1$–$C_{10}$-alkyl)$_4^+$, and N(H/$C_1$–$C_{10}$-alkyl/$C_6$–$C_{10}$-aryl)$_4^+$.

14. A process according to claim 12, wherein the substituents of the aryl groups are π-bonded metal complexes of the formulae (IV) or (V),

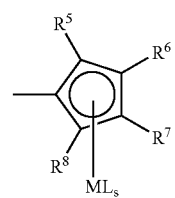

(IV)

-continued

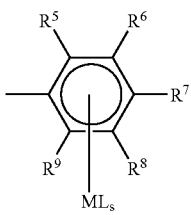

(V)

wherein s denotes integers in the range of 1 to 6 and

M denotes chromium, molybdenum, tungsten, manganese, rhenium, iron, cobalt, nickel or an element from the lanthanide series and $R^5$ to $R^9$ are the same or different and correspond to one of the residues defined for $R^3$–$R^4$ and wherein the ligands $L_1$ to $L_S$ are the same or different and denote a cyclic ether with 5–6 ring atoms, a cyclic olefin with 5–8 ring atoms, pyridine, CO, $PF_3$ or a ligand of general formulae

 (VI)

 (VII):

wherein $L^1$ and $L^2$, independently of one another, denotes a coordinating group of formulae (VIII), (IX), (X), (XI) or (XII):

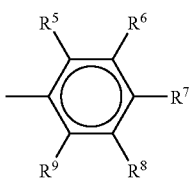 (VIII)

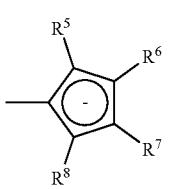 (IX)

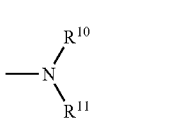 (X)

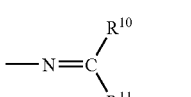 (XI)

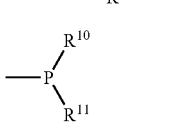 (XII)

wherein $R^5$ to $R^9$, independently of one another, are selected from the group consisting of hydrogen, $(C_1–C_{24})$-alkyl, $(C_2–C_{24})$-alkenyl, $(C_2–C_{24})$-alkynyl, $(C_5–C_{10})$-aryl, $CF_3$, CO-alkyl-$(C_1–C_8)$, CO-aryl-$(C_5–C_{10})$, CN, COOH, COOM, COO-alkyl-$(C_1–C_8)$, COO-aryl-$(C_5–C_{10})$, C(=N-alkyl-$(C_1–C_8)$)O-alkyl-$(C_1–C_8)$, C(=N-aryl-$(C_5–C_{10})$)(O-alkyl-$(C_1–C_8)$), C(=N-alkyl-$(C_1–C_8)$)(O-aryl-$(C_5–C_{10})$), C(=N-aryl-$(C_5–C_{10})$)(O-aryl-$(C_5–C_{10})$), $CONH_2$, CONH-alkyl-$(C_1–C_8)$, CON(alkyl-$(C_1–C_8))_2$, CONH-aryl-$(C_5–C_{10})$, CON(aryl-$(C_5–C_{10}))_2$, PO(aryl-$(C_5–C_{10}))_2$, PO(alkyl-$(C_1–C_4))_2$, POH(alkyl-$(C_1–C_6)$), POH(aryl-$(C_5–C_{10})$), PO(alkyl-$(C_1–C_4)$)(O-alkyl-$(C_1–C_6)$), PO(alkyl-$(C_1–C_6)$)(O-aryl-$(C_5–C_{10})$), PO(aryl-$(C_5–C_{10})$)(O-alkyl-$(C_1–C_6)$), $PO_3H_2$, $PO_3M_2$, PO(O-alkyl-$(C_1–C_6))_2$, PO(O-aryl-$(C_5–C_{10}))_2$, PO(O-alkyl-$(C_1–C_6)$)(O-aryl-$(C_5–C_{10})$), $SO_3H$, $SO_3M$, $SO_3$-alkyl-$(C_1–C_4)$, $SO_3$-aryl-$(C_5–C_{10})$, $SO_2$-alkyl-$(C_1–C_6)$, $SO_2$-aryl-$(C_5–C_{10})$, SO-alkyl-$(C_1–C_8)$, SO-aryl-$(C_5–C_{10})$, S-alkyl-$(C_1–C_8)$, S-aryl-$(C_5–C_{10})$, SH, Si(alkyl-$(C_1–C_8))_3$, Si($C_1–C_{10}$-alkyl/$C_5–C_{10}$-aryl$)_3$, $NO_2$, F, Cl, Br, I, O-alkyl-$(C_1–C_8)$, O-aryl-$(C_5–C_{10})$, OH, $NH_2$, NH(alkyl-$(C_1–C_8)$), N(alkyl-$(C_1–C_8))_2$, NH(aryl-$(C_5–C_{10})$), NHCO-alkyl-$(C_1–C_4)$, NHCO-aryl-$(C_5–C_{10})$, NHCOO-alkyl-$(C_1–C_4)$, NHCOO-aryl-$(C_5–C_{10})$, OCO-alkyl-$(C_1–C_8)$, OCO-aryl-$(C_5–C_{10})$, OPO(aryl-$(C_5–C_{10}))_2$, OPO(alkyl-$(C_1–C_4))_2$, OPOH(alkyl-$(C_1–C_6)$), $OPO_3H_2$, $OPO_3M_2$, OPO-alkyl-$(C_1–C_4)$(O-alkyl-$(C_1–C_6)$), OPO(O-alkyl-$(C_1–C_6))_2$, OPO(O-aryl-$(C_5–C_{10}))_2$, $OSO_3H$, $OSO_3M$, $OSO_2$–$CF_3$, $OSO_3$-alkyl-$(C_1–C_4)$, $OSO_3$-aryl-$(C_5–C_{10})$, $OSO_2$-alkyl-$(C_1–C_6)$, and $OSO_2$-aryl-$(C_5–C_{10})$, wherein M represents a cation selected from the group consisting of $Li^+$, $Na^+$, $K^+$, $Mg^{2+}$, $Ca^{2+}$, $NH_4^+$, $N(C_1–C_{10}$-alkyl$)_4^+$, and $N(C_1–C_{10}$-alkyl/$C_5–C_{10}$-aryl$)_4^+$, and wherein the residues $R^{10}$ to $R_{12}$, independently of one another, represent a hydrogen, $(C_1–C_{24})$-alkyl, $(C_2–C_{24})$-alkenyl, $(C_2–C_{24})$-alkynyl, $C_5–C_8$cycloalkenyl, $(C_5–C_{14})$-aryl, O-alkyl-$(C_1–C_8)$, O-aryl-$(C_5–C_{14})$, O-alkenyl-$(C_2–C_{24})$, O-alkynyl-$(C_2–C_{24})$, O-cycloalkenyl-$(C_5–C_8)$, O-aryl-$(C_5–C_{14})$, F, $NH_2$, NH(alkyl-$(C_1–C_8)$), NH-alkenyl-$(C_2–C_{24})$, NH-alkynyl-$(C_2–C_{24})$, NH-cycloalkenyl-$(C_5–C_8)$, NH-aryl-$(C_5–C_{14})$, N(alkyl-$(C_1–C_8))_2$, N(alkenyl-$(C_2–C_{24}))_2$, N(alkynyl-$(C_2–C_{24}))_2$, N(cycloalkenyl-$(C_5–C_8))_2$, N(alkyl-$(C_1–C_8)$)(aryl-$(C_5–C_{10})$), N(aryl-$(C_5–C_{10}))_2$, NHCO-alkyl-$(C_1–C_4)$, NHCO-alkenyl-$(C_2–C_{24})$, NHCO-alkynyl-$(C_2–C_{24})$, NHCO-cycloalkenyl-$(C_5–C_8)$, NHCO-aryl-$(C_5–C_{14})$, OCO-alkyl-$(C_1–C_4)$, OCO-alkenyl-$(C_2–C_{24})$, OCO-cycloalkenyl-$(C_5–C_8)$, OCO-aryl-$(C_5–C_{14})$, or $SO_2$-alkyl-$(C_1–C_6)$, $SO_2$-aryl-$(C_5–C_{10})$ residue and wherein all the above-mentioned substituents are optionally mono- or polysubstituted, and wherein two adjacent residues together optionally form saturated or unsaturated carbocyclic or heterocyclic groups having 3 to 15 atoms, with one to four nitrogen, phosphorus, silicon, sulfur or oxygen atoms, and wherein Q represents a bridge linking the unit $L^1$ with the unit $L^2$, of formula (XIII):

$$X^1—Z—X^2 \quad (XIII)$$

wherein $X^1$ and $X^2$, independently of one another, represent a direct bond or a group —O—, —S—, or —$NR^{13}$—, wherein $R^{13}$ is one of the residues defined for $R^{10}$–$R^{12}$ and Z is a direct bond or a group of 1–16 carbon atoms linked by single or multiple bonds, wherein one to four carbon atoms are optionally replaced by heteroatoms, and wherein Z is optionally mono- or polysubstituted as stated for $R^5$–$R^9$ or optionally has a keto (═O), thioketo (═S) or imide substituent (═$NR^{14}$), wherein $R_{14}$ is one of the residues defined for $R_{10}$–$R_{12}$ and wherein two of the units $L^1$ with $R^{12}$ and $L^1$ or $L^2$ with Q are optionally linked together so that a saturated or unsaturated carbocyclic skeleton having 3 to 15 atoms or a saturated or unsaturated heterocyclic skeleton containing one to four nitrogen, phosphorus, silicon, sulfur or oxygen atoms is formed.

15. A process according to claim 1, wherein the transition metal complex catalyst is used in a quantity of between 0.001 and 10 mole %, based on the carbonyl compound.

16. A process according to claim 3, wherein the transition metal complex catalyst has a ratio between metal precursor and ligand of formula (VI) or (VII) of 1:0.01 to 1:50.

17. A process according to claim 1, wherein the reaction is performed at temperatures of between −78° C. and 150° C.

18. A process according to claim 15, wherein the transition metal complex catalyst contains at least one ligand selected from the group consisting of:

(1) mono- or bidentate nitrogen donor ligands, phosphorus donor ligands, cyclopentadienyl ligands, arene ligands, olefin ligands, alkyne ligands, heterocycloalkyl ligands, heteroaryl ligands, hydride ligands, alkyl ligands, carbonyl ligands and a mixture of these ligands;

(2) at least one mono- or bidentate ligand of formula (VI) or (VII), $$L^1 13 \quad L^{12} \tag{VI}$$

$$L^1—Q—L^2 \tag{VII}$$

wherein $L^1$ and $L^2$, independently of one another, denote a coordinating group of formulae (VIII), (IX), (X), (XI) or (XII):

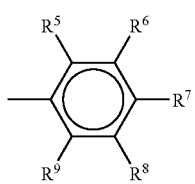
(VIII)

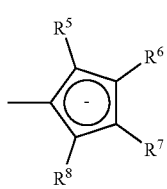
(IX)

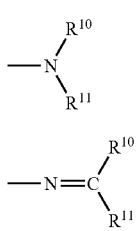
(X)

(XI)

(XII)

wherein $R^5$ to $R^9$, independently of one another, are selected from the group consisting of hydrogen, ($C_1$–$C_{24}$)-alkyl, ($C_2$–$C_{24}$)-alkenyl, ($C_2$–$C_{24}$)-alkynyl, ($C_5$–$C_{10}$)-aryl, $CF_3$, CO-alkyl-($C_1$–$C_8$), CO-aryl-($C_5$–$C_{10}$), CN, COOH, COOM, COO-alkyl-($C_1$–$C_8$), COO-aryl-($C_5$–$C_{10}$), C(═N-alkyl-($C_1$–$C_8$))O-alkyl-($C_1$–$C_8$), C(═N-aryl-($C_5$–$C_{10}$))(O-alkyl-($C_1$–$C_8$)), C(═N-alkyl-($C_1$–$C_8$))(O-aryl-($C_5$–$C_{10}$)), C(═N-aryl-($C_5$–$C_{10}$))(O-aryl-($C_5$–$C_{10}$)), $CONH_2$, CONH-alkyl-($C_1$–$C_8$), CON(alkyl-($C_1$–$C_8$))$_2$, CONH-aryl-($C_5$–$C_{10}$), CON(aryl-($C_5$–$C_{10}$))$_2$, PO(aryl-($C_5$–$C_{10}$))$_2$, PO(alkyl-($C_1$–$C_4$))$_2$, POH(alkyl-($C_1$–$C_6$)), POH(aryl-($C_5$–$C_{10}$)), PO(alkyl-($C_1$–$C_4$))(O-alkyl-($C_1$–$C_6$)), PO(alkyl-($C_1$–$C_6$))(O-aryl-($C_5$–$C_{10}$)), PO(aryl-($C_5$–$C_{10}$))(O-alkyl-($C_1$–$C_6$)), $PO_3H_2$, $PO_3M_2$, PO(O-alkyl-($C_1$–$C_6$))$_2$, PO(O-aryl-($C_5$–$C_{10}$))$_2$, PO(O-alkyl-($C_1$–$C_6$))(O-aryl-($C_5$–$C_{10}$)), $SO_3H$, $SO_3M$, $SO_3$-alkyl-($C_1$–$C_4$), $SO_3$-aryl-($C_5$–$C_{10}$), $SO_2$-alkyl-($C_1$–$C_6$), $SO_2$-aryl-($C_5$–$C_{10}$), SO-alkyl-($C_1$–$C_8$), SO-aryl-($C_5$–$C_{10}$), S-alkyl-($C_1$–$C_8$), S-aryl-($C_5$–$C_{10}$)., SH, Si(alkyl-($C_1$–$C_8$))$_3$, Si($C_1$–$C_{10}$-alkyl/$C_5$–$C_{10}$-aryl)$_3$, $NO_2$, F, Cl, Br, I, O-alkyl-($C_1$–$C_8$), O-aryl-($C_5$–$C_{10}$), OH, $NH_2$, NH(alkyl-($C_1$–$C_8$)), N(alkyl-($C_1$–$C_8$))$_2$, NH(aryl-($C_5$–$C_{10}$)), NHCO-alkyl-($C_1$–$C_4$), NHCO-aryl-($C_5$–$C_{10}$), NHCOO-alkyl-($C_1$–$C_4$), NHCOO-aryl-($C_5$–$C_{10}$), OCO-alkyl-($C_1$–$C_8$), OCO-aryl-($C_5$–$C_{10}$), OPO(aryl-($C_5$–$C_{10}$))$_2$, OPO(alkyl-($C_1$–$C_4$))$_2$, OPOH(alkyl-($C_1$–$C_6$)), $OPO_3H_2$, $OPO3M_2$, OPO-alkyl-($C_1$–$C_4$)(O-alkyl-($C_1$–$C_6$)), OPO(O-alkyl-($C_1$–$C_6$))$_2$, OPO(O-aryl-($C_5$–$C_{10}$))$_2$, $OSO_3H$, $OSO_3M$, $OSO_2$—$CF_3$, $OSO_3$-alkyl-($C_1$–$C_4$), $OSO_3$-aryl-($C_5$–$C_{10}$), $OSO2$-alkyl-($C_1$–$C_6$), and $OSO_2$-aryl-($C_5$–$C_{10}$), wherein M represents a cation selected from the group consisting of $Li^+$, $Na^+$, $K^+$, $Mg^{2+}$, $Ca^{2+}$, $NH_4^+$, N($C_1$–$C_{10}$-alkyl)$_4^+$, and N($C_1$–$C_{10}$-alkyl/$C_5$–$C_{10}$-aryl)$_4^+$, and wherein the residues $R^{10}$ to $R_{12}$, independently of one another, represent a hydrogen, ($C_1$–$C_{24}$)-alkyl, ($C_2$–$C_{24}$)-alkenyl, ($C_2$–$C_{24}$)-alkynyl, $C_5$–$C_8$cycloalkenyl, ($C_5$–$C_{14}$)-aryl, O-alkyl-($C_1$–$C_8$), O-aryl-($C_5$–$C_{10}$), O-alkenyl-($C_2$–$C_{24}$), O-alkynyl-($C_2$–$C_{24}$), O-cycloalkenyl-($C_5$–$C_8$), O-aryl-($C_5$–$C_{14}$), F, $NH_2$, NH(alkyl-($C_1$–$C_8$)), NH-alkenyl-($C_2$–$C_{24}$), NH-alkynyl-($C_2C_{24}$), NH-cycloalkenyl-($C_5$–$C_8$), NH-aryl-($C_5$–$C_{14}$), N(alkyl-($C_1$–$C_8$))$_2$, N(alkenyl-($C_2$–$C_{24}$))$_2$, N(alkynyl-($C_2$–$C_{24}$))$_2$, N(cycloalkenyl-($C_5$–$C_8$))$_2$, N(alkyl-($C_1$–$C_8$))(aryl-($C_5$–$C_{10}$)), N(aryl-($C_5$–$C_{10}$))$_2$, NHCO-alkyl-($C_1$–$C_4$), NHCO-alkenyl-($C_2$–$C_{24}$), NHCO-alkynyl-($C_2$–$C_{24}$), NHCO-cycloalkenyl-($C_5$–$C_8$), NHCO-aryl-($C_5$–$C_{14}$), OCO-alkyl-($C_1$–$C_4$), OCO-alkenyl-($C_2$–$C_{24}$), OCO-cycloalkenyl-($C_5$–$C_8$), OCO-aryl-($C_5$–$C_{14}$), or $SO_2$-alkyl-($C_1$–$C_6$), $SO_2$-aryl-($C_5$–$C_{10}$) residue and wherein all the above-mentioned substituents are optionally mono- or polysubstituted, and wherein two adjacent residues together optionally form saturated or unsaturated carbocyclic or heterocyclic groups having 3 to 15 atoms, with one to four nitrogen, phosphorus, silicon, sulfur or oxygen atoms, and wherein Q represents a bridge linking the unit $L^1$ with the unit $L^2$, of formula (XIII):

$$X^1 \text{---} Z \text{---} X^2 \quad \quad (XIII)$$

wherein $X^1$ and $X^2$, independently of one another, represent a direct bond or a group —O—, —S—, or —$NR^{13}$—, wherein $R^{13}$ is one of the residues defined for $R^{10}$–$R^{12}$ and Z is a direct bond or a group of 1–16 carbon atoms linked by single or multiple bonds, wherein one to four carbon atoms are optionally replaced by heteroatoms, and wherein Z is optionally mono- or polysubstituted as stated for $R^5$–$R^9$ or optionally has a keto (=O), thioketo (=S) or imide substituent (=$NR^{14}$), wherein $R^{14}$ is one of the residues defined for $R^{10}$–$R^{12}$ and wherein two of the units $L^1$ with $R^{12}$ and $L^1$ or $L^2$ with Q are optionally linked together so that a saturated or unsaturated carbocyclic skeleton having 3 to 15 atoms or a saturated or unsaturated heterocyclic skeleton containing one to four nitrogen, phosphorus, silicon, sulfur or oxygen atoms is formed; and (3) at least one mono-, bi-, tri- or tetradentate linear, branched or polycyclic, alkyne, olefin, conjugated or non-conjugated di- tri- or tetraene with two to twelve carbon atoms, wherein one to four carbon atoms are optionally replaced with nitrogen or silicon atoms or one to two carbon atoms are optionally replaced with oxygen or sulfur atoms and wherein the individual members of the group, independently of one another, optionally have substituents as defined for $R^5$–$R^9$ or a keto (=O), thioketo (=S) or imide substituent (=$NR^{14}$), wherein $R^{14}$ is one of the residues defined for $R^{10}$–$R^{12}$.

19. A process according to claim 18, wherein Q in formula (VII) represents an aliphatic, olefinic or acetylenic bridge consisting of one to fourteen carbon atoms, wherein one to four carbon atoms are optionally replaced with nitrogen or silicon atoms or one to two carbon atoms are optionally replaced with oxygen or sulfur atoms and wherein the individual binding links of the group, independently of one another, optionally carry substituents as defined for $R^3$ and $R^4$ or a keto (=O), thioketo (=S) or imide substituent (=$NR^{14}$) wherein $R^{14}$ is one of the residues defined for $R^{10}$–$R^{12}$ and wherein two of the units $L^1$, $L^2$ and Q are optionally linked together so that a saturated or unsaturated carbocyclic skeleton having 5 to 9 atoms or a saturated or unsaturated, heterocyclic skeleton containing one to four nitrogen, phosphorus, silicon, sulfur or oxygen atoms is formed; wherein $R^3$ and $R^4$, independently of one another are each selected from the group consisting of hydrogen, ($C_1$–$C_{24}$)-alkyl, ($C_2$–$C_{24}$)-alkenyl, ($C_2$–$C_{24}$)-alkynyl, ($C_5$–$C_{10}$)-aryl, $CF_3$, CHO, CO-alkyl-($C_1$–$C_8$), CO-aryl-($C_5$–$C_{10}$), COO-alkyl-($C_1$–$C_8$), COO-aryl-($C_5$–$C_{10}$), C(=N-alkyl-($C_1$–$C_8$))O-alkyl-($C_1$–$C_8$), C(=N-aryl-($C_6$–$C_{10}$))O-alkyl-($C_1$–$C_8$), C(=N-alkyl-($C_1$–$C_8$))O-aryl-($C_5$–$C_{10}$), C(=N-aryl-($C_5$–$C_{10}$)) O-aryl-($C_5$–$C_{10}$), $CONH_2$, CONH-alkyl-($C_1$–$C_8$), CON(alkyl-($C_1$–$C_8$))$_2$, CONH-aryl-($C_5$–$C_{10}$), CON(aryl-($C_5$–$C_{10}$))$_2$, PO(aryl-($C_5$–$C_{10}$))$_2$, PO(alkyl-($C_1$–$C_4$))$_2$, PO(alkyl-($C_1$–$C_4$))(O-alkyl-($C_1$–$C_6$)), PO(alkyl-($C_1$–$C_6$))(O-aryl-($C_5$–$C_{10}$))(O-alkyl-($C_1$–$C_6$)), PO(O-alkyl-($C_1$–$C_6$))$_2$, PO(O-aryl-($C_5$–$C_{10}$))$_2$, PO(O-alkyl-($C_1$–$C_6$))(O-aryl-($C_5$–$C_{10}$)), $SO_2$—O-alkyl-($C_1$–$C_4$), $SO_2$—O-aryl-($C_5$–$C_{10}$)$_2$-alkyl-($C_1$–$C_6$), $SO_2$-aryl-($C_5$–$C_{10}$), SO-alkyl-($C_1$–$C_8$), SO-aryl-($C_5C_{10}$), or Si(alkyl-($C_1$–$C_8$))$_3$, and Si($C_1$–$C_{10}$-alkyl/$C_5$–$C_{10}$-aryl)$_3$, O-alkyl-($C_1$–$C_8$), O-aryl-($C_5$–$C_{10}$), fluorine, OH, $NH_2$, NH(alkyl-($C_1$–$C_8$)), N(alkyl-($C_1$–$C_8$))$_2$, NH(aryl-($C_5$–$C_{10}$)), NHCO-alkyl-($C_1$–$C_4$), NHCO-aryl-($C_5$–$C_{10}$), NHCOO-alkyl-(C1–$C_8$), and NHCOO-aryl-($C_5$–$C_{10}$), wherein alkyl denotes a linear or branched, aliphatic or cyclic residue, alkenyl denotes an olefinic hydrocarbon, alkynyl denotes an acetylene hydrocarbon and aryl denotes an aromatic residue, wherein upto 4 carbon atoms in each case are optionally replaced by a nitrogen, phosphorus, silicon, sulfur or oxygen atom, further wherein $R^3$ and $R^4$ are optionally linked by covalent bonds, so that $R^3$ and $R^4$ optionally each form a saturated or unsaturated carbocyclic or heterocyclic unit having 3 to 15 atoms, with one to four nitrogen, phosphorus, silicon, sulfur or oxygen atoms.

* * * * *